(12) United States Patent
Samaddar et al.

(10) Patent No.: US 8,999,897 B2
(45) Date of Patent: Apr. 7, 2015

(54) PROTEIN TAG COMPRISING A BIOTINYLATION DOMAIN AND METHOD FOR INCREASING SOLUBILITY AND DETERMINING FOLDING STATE

(75) Inventors: Mitali Samaddar, Andhra Pradesh (IN); Jonathan Michael Blackburn, Cambridge (GB); Darren James Hart, Grenoble (FR); Michael Richard Dyson, Great Shelford (GB)

(73) Assignee: Sense Proteomic Limited, Oxford (GB)

( * ) Notice: Subject to any disclaimer, the term of this patent is extended or adjusted under 35 U.S.C. 154(b) by 564 days.

(21) Appl. No.: 10/502,581

(22) PCT Filed: Jan. 29, 2003

(86) PCT No.: PCT/GB03/00362
§ 371 (c)(1),
(2), (4) Date: Mar. 30, 2005

(87) PCT Pub. No.: WO03/064656
PCT Pub. Date: Aug. 7, 2003

(65) Prior Publication Data
US 2005/0221308 A1    Oct. 6, 2005

(30) Foreign Application Priority Data

Jan. 29, 2002    (GB) .................................. 0202018.8

(51) Int. Cl.

| | | |
|---|---|---|
| C40B 40/10 | (2006.01) | |
| C40B 30/10 | (2006.01) | |
| C40B 40/06 | (2006.01) | |
| C40B 50/00 | (2006.01) | |
| C40B 20/04 | (2006.01) | |
| C12N 9/00 | (2006.01) | |
| C12N 15/62 | (2006.01) | |
| C12N 15/67 | (2006.01) | |
| C12P 21/02 | (2006.01) | |

(52) U.S. Cl.
CPC ........ *C12N 9/93* (2013.01); *C12N 15/62* (2013.01); *C12N 15/67* (2013.01); *C12P 21/02* (2013.01); *C07K 2319/23* (2013.01); *C07K 2319/60* (2013.01); *C07K 2319/90* (2013.01)

(58) Field of Classification Search
USPC ...................................... 506/4, 12, 16, 18, 23
See application file for complete search history.

(56) References Cited

U.S. PATENT DOCUMENTS

| | | | | |
|---|---|---|---|---|
| 5,252,466 | A * | 10/1993 | Cronan, Jr. .................... | 435/69.7 |
| 5,723,584 | A * | 3/1998 | Schatz .......................... | 530/408 |
| 5,801,233 | A * | 9/1998 | Haselkorn et al. ............ | 536/23.6 |
| 5,814,465 | A * | 9/1998 | Tatsumi et al. ................ | 435/7.5 |
| 5,932,433 | A | 8/1999 | Schatz ............................ | 435/15 |
| 7,148,058 | B2 * | 12/2006 | Charych et al. ............. | 435/287.8 |
| 7,816,098 | B2 | 10/2010 | Blackburn et al. | |
| 2003/0228709 | A1 | 12/2003 | Kozlowski et al. | |
| 2004/0002078 | A1 | 1/2004 | Boutell et al. | |
| 2005/0181449 | A1 | 8/2005 | Kozlowski et al. | |
| 2006/0024791 | A1 | 2/2006 | Kozlowski et al. | |
| 2011/0172123 | A1 | 7/2011 | Kozlowski et al. | |

FOREIGN PATENT DOCUMENTS

| | | |
|---|---|---|
| EP | 0511747 | 11/1992 |
| WO | WO 90/14431 | 11/1990 |
| WO | WO 95/25172 | 9/1995 |
| WO | WO-0129220 A2 | 4/2001 |
| WO | WO 01/57198 | 8/2001 |
| WO | WO 02/27327 | 4/2002 |
| WO | WO-02064796 A2 | 8/2002 |
| WO | WO-02099099 A2 | 12/2002 |
| WO | WO 03/064656 | 8/2003 |

OTHER PUBLICATIONS

Germino et al., Screening for in vivo protein-protien interactions, Feb. 1993, PNAS, 90, pp. 933-937.*
Jasper, Structures of MBP, website at ftns.wau.nl/micr/bacgen/jasper, one page, 2007.*
Cronan, *The Journal of Biological Chemistry*, 266:10327-10333 (1990).
Germino, et al., *Proceedings of the National Academy of Science*, 90:933-937 (1993).
Jager, et al., *Archives of Microbiology*, 166:76-82 (1996).
Murtif, et al., *Journal of Biological Chemistry*, 262:11813-11816 (1987).
Rao, et al., *Nature*, 410: 955-959; (2001).
*Gene*, Elsevier Biomedical Press., 173:147-154 (1996), Wang et al.
International Search Report, PCT/GB03/00362, dated Jul. 2, 2003, see note in action.
Stephen and Lane, "Mutant Conformation of p3: Precise Epitope Mapping Using a Filamentous Phage Epitope Library", *J. Mol. Biol.*, 225:577-583 (1992).
Toepert et al., "Synthesis of an Array Comprising 837 Variants of the hYAP WW Protein Domain", *Angew. Chem. Int. Ed.*, 40:897-900 (2001).

* cited by examiner

*Primary Examiner* — Amber D Steele
(74) *Attorney, Agent, or Firm* — Wenderoth, Lind & Ponack, L.L.P.

(57) ABSTRACT

The use of a tag moiety comprising a biotinylation domain, such as biotin carboxyl carrier protein (BCCP), as a protein folding marker and protein solubility enhancer in the orientated surface capture of products of heterologously expressed genes is described. Methods for increasing the solubility of proteins and determining the folded state of a protein are also disclosed. The uses and methods of the invention can be carried out in a multiplexed manner on more than one protein in the formation of libraries. In addition the nucleic acid molecule encoding the biotinylation domain of the tag moiety can be used to increase the proportion of clones in a library that express the protein of interest.

10 Claims, 12 Drawing Sheets

Probe: Strep.-HRP conjugate pIFM101A

EcoRI                                                              DraIII

61  ATTGTGAGCG GATAACAATT TCACACAGAA TTCATTAAAG AGGAGAAATT AACTATGCAC
    TAACACTCGC CTATTGTTAA AGTGTGTCTT AAGTAATTTC TCCTCTTTAA TTGATACGTG
                                                                 GFP

DraIII        SphI          XmaI
          BamHI         SacI          SmaI
121 TTAGTGGGAT CCGCATGCGA GCTCGGTACC CCGGGCCGGT GGCAGCGCGA GTAAAGGAGA
    AATCACCCTA GGCGTACGCT CGAGCCATGG GGCCCGGCCA CCGTCGCGCT CATTTCCTCT
                                GFP

181 AGAACTTTTC ACTGGAGTTG TCCCAATTCT TGTTGAATTA GATGGTGATG TTAATGGGCA
    TCTTGAAAAG TGACCTCAAC AGGGTTAAGA ACAACTTAAT CTACCACTAC AATTACCCGT

FIG. 10 pIFM101B

EcoRI                                                              DraIII

61  ATTGTGAGCG GATAACAATT TCACACAGAA TTCATTAAAG AGGAGAAATT AACTATGGCA
    TAACACTCGC CTATTGTTAA AGTGTGTCTT AAGTAATTTC TCCTCTTTAA TTGATACCGT
                                                                 GFP

DraIII        SphI          XmaI
          BamHI         SacI          SmaI
121 CTTAGTGGGA TCCGCATGCG AGCTCGGTAC CCCGGGCCGG TGGCAGCGCG AGTAAAGGAG
    GAATCACCCT AGGCGTACGC TCGAGCCATG GGGCCCGGCC ACCGTCGCGC TCATTTCCTC
                                GFP

181 AAGAACTTTT CACTGGAGTT GTCCCAATTC TTGTTGAATT AGATGGTGAT GTTAATGGGC
    TTCTTGAAAA GTGACCTCAA CAGGGTTAAG AACAACTTAA TCTACCACTA CAATTACCCG

FIG. 11 pIFM101C

```
                EcoRI                                              DraIII
                ~~~~~~~                                              ~
 61 ATTGTGAGCG GATAACAATT TCACACAGAA TTCATTAAAG AGGAGAAATT AACTATGGAC
    TAACACTCGC CTATTGTTAA AGTGTGTCTT AAGTAATTTC TCCTCTTTAA TTGATACCTG
                                                            GFP
                                                            ~~~~~~~~~~~~

DraIII        SphI                 XmaI
       ~~~~~~~       ~~~~~~               ~~~~~~
             BamHI         SacI     SmaI
             ~~~~~~~       ~~~~~~   ~~~~~~
121 ACTTAGTGGG ATCCGCATGC GAGCTCGGTA CCCCGGGCCG GTGGCAGCGC GAGTAAAGGA
    TGAATCACCC TAGGCGTACG CTCGAGCCAT GGGGCCCGGC CACCGTCGCG CTCATTTCCT
                                      GFP
    ~~~~~~~~~~~~~~~~~~~~~~~~~~~~~~~~~~~~~~~~~~~~~~~~~~~~~~~~~~~~~~~~

181 GAAGAACTTT TCACTGGAGT TGTCCCAATT CTTGTTGAAT TAGATGGTGA TGTTAATGGG
    CTTCTTGAAA AGTGACCTCA ACAGGGTTAA GAACAACTTA ATCTACCACT ACAATTACCC
```

FIG. 12

PROTEIN TAG COMPRISING A BIOTINYLATION DOMAIN AND METHOD FOR INCREASING SOLUBILITY AND DETERMINING FOLDING STATE

This invention relates to the use of biotin carboxyl carrier protein (BCCP) as a protein folding marker and protein solubility enhancer in the orientated surface capture of products of heterologously expressed genes.

Expression of human proteins in heterologous systems such as bacteria, yeast, insect cells or mammalian cells can result in the production of incorrectly folded proteins resulting in the formation of insoluble aggregates or a low yield of expressed proteins because of the targeting of the unfolded proteins to the proteosome. For all functional protein procedures the production of correctly folded or native proteins is essential and a great deal of work is often performed to optimise the expression of individual proteins. However, many areas of protein biochemistry involve working with libraries or groups of proteins of such a size that optimisation of individual expression and purification conditions for each protein is impractical. Hence, there exists an unmet need in the art for reagents, protocols and methodology that facilitate the multiplexing of these processes.

Affinity tags are a convenient method of purification and immobilisation of recombinant proteins. Hexahistidine tags (6 amino acids (aa); Qiagen/Roche), *Escherichia coli* maltose binding protein ("MBP", 300 aa; New England Biolabs) and *Schistosoma japonicum* glutathione-S-transferase (GST, 220 aa; Amersham Pharmacia Biotech/Novagen) are effective, but have the disadvantage that heterologous host proteins interact with the affinity matrices used for purification of fusion proteins. This results in impure protein preparations and an additional clean up step is often required. Additionally, the relatively weak affinity of these proteins for their ligands results in dissociation, or "leaching" of the fusion proteins from surfaces to which they are immobilised. Such reversible interactions are exploited during resin-based purifications on resins in column or batch formats where, because of the high local concentrations of ligand, dissociated proteins rapidly rebind, yet are rapidly eluted by free ligand. In contrast, immobilisation of proteins to planar surfaces such as microtiter plates or microarrays, for example, biochips, requires that they remain bound and do not leach from the substrate during storage and use. As such, lower affinity tags as used for purification (e.g. MBP, GST and hexahistidine tags) are suboptimal. Frequently, covalent immobilisation strategies are employed such as coupling of purified proteins via surface lysine residues to amine-reactive chemical groups. This is generally accepted to result in reduced activity of the protein.

In contrast to the lower affinity, non-covalent interactions described above, the interaction of biotin with streptavidin, avidin or deglycosylated avidin NEUTRAVIDINT™, Thermo Scientific, Rockford, Ill.) exhibits some of the highest affinities known in biology, with equilibrium dissociation constants of $10^{-15}$ M (several orders of magnitude higher affinity than the MBP—amylose or GST—glutathione interactions). Whilst still a weaker interaction than covalent coupling, biotinylated proteins bound to a streptavidin-derivatised surface show negligible dissociation. This interaction therefore provides an improved means for tethering proteins to a planar surface for applications such as protein arrays and enzyme-linked immunoassays (ELISAs).

Biotin can be attached chemically to proteins (e.g. using NHS-activated biotin), or via genetically fused protein domains which are biotinylated in vivo. The "PinPoint™" vectors from Promega are designed to facilitate the creation of fusions to the biotinylation domain (which is a fragment of the biotin carboxyl carrier protein (BCCP) of methylmalonyl-CoA carboxyl transferase from *Propionibacterium freudenreichii shermanii* [U.S. Pat. No. 5,252,466]). This protein has 40% homology with the *E. coli* BCCP. This system allows the production of BCCP-protein fusions capable of being biotinylated either in vivo or in vitro by biotin ligase, allowing one to use the highly specific biotin—streptavidin interaction for surface capture. In addition to the BCCP domain, phage display selected short peptides capable of being biotinylated on a lysine residue have been commercialised by Avidity Inc. [U.S. Pat. No. 5,932,433].

The Inventors herein describe a novel approach whereby BCCP from *E. coli* is fused either N- or C-terminally to a protein partner. In addition to the function of permitting orientated immobilization of the fusion protein to microarray compatible surfaces derivatised with avidin, streptavidin or deglycosylated avidin (NEUTRAVIDIN™, Thermo Scientific, Rockford, Ill.), the Inventors describe new, previously unreported functions of BCCP which greatly facilitate the creation of libraries of solubly expressed folded human, mammalian, fungal, plant or microbial proteins in heterologous systems.

i) N-Terminally or C-Terminally Fused BCCP Improves Levels of Folding of Fusion Partner The factors determining the solubility of recombinant proteins are poorly understood and so rational design of solubility and increased expression into recombinant proteins is only possible to a limited extent. However, by fusing well expressed soluble proteins to the N-terminus of a protein, both properties can be greatly improved compared with expression of ORFs alone. Examples include MBP, GST and thioredoxin (Trx, 109 aa; Novagen). A possible mechanism of action is thought to be the recruitment of chaperones to the nascent polypeptide and co-over-expression of chaperones can result in increased yield of soluble protein. Some fusion proteins can then be purified via their fusion protein domain (e.g. amylose resin for MBP or glutathione resin for GST. Although the Trx tag has not been used for protein purification it can both improve the solubility of many target proteins and it appears to catalyse the formation of disulphide bonds in the cytoplasm of *E. coli* trx B mutants.

The Inventors have determined that addition of BCCP to the N-terminus or C-terminus of a protein increases the solubility of the fusion protein and in the case of addition to the N-terminus at least, increases the proportion of clones in a library that express encoded proteins (relative to a library that is not modified to also encode a BCCP tag). Additionally, the BCCP domain is biotinylated in vivo. This is particularly useful when attempting to multiplex protein purification for fabrication of protein arrays since the proteins can be simultaneously purified from cellular lysates and immobilised in a single step via the high affinity and specificity exhibited by a streptavidin surface. The Inventors term this simultaneous purification and immobilisation as "surface capture".

ii) N-Terminally or C-Terminally Fused BCCP Permits Monitoring of Folding of Fusion Partner Fusion of reporter proteins (with an assayable activity) onto the C-terminus of partner proteins has been previously shown to allow monitoring of the folding of the partner. Notable examples of reporter systems known in the art utilise green fluorescent protein (GFP), chloramphenicol acetyl transferase (CAT), β-galactosidase and the α-complementation of β-galactosidase.

The Inventors have determined that addition of BCCP to the N-terminus or C-terminus of a protein permits the monitoring of fusion protein folding by measuring the extent of in vivo biotinylation. This can be measured by standard blotting procedures, using SDS-PAGE or in situ colony lysis and transfer of samples to a membrane, followed by detection of biotinylated proteins using a streptavidin conjugate such as streptavidin-horseradish peroxidase. Importantly, the addition of biotin to the BCCP domain permits purification by surface capture as described above.

Thus in a first aspect the invention provides the use of a tag moiety comprising a biotinylation domain for increasing the solubility of a protein of interest by attachment of said tag moiety to the N-terminal or C-terminus of said protein of interest.

A tag moiety comprising a biotinylation domain as defined herein is an amino acid sequence comprising a protein or protein domain which is capable of being biotinylated, or to which a biotin group can be attached. In accordance with the first aspect of the invention the tag is highly soluble in the cytoplasm of the host cell in which it is expressed as a tag attached to a protein of interest.

Essentially, the biotinylation domain of the invention is a protein or protein domain having secondary and tertiary structure and which is biotinylated in vivo post translationally. Generally the secondary and tertiary structure of the protein or domain is essential for recognition and hence biotinylation by the biotin ligase of the host cell in which expression of the tag is taking place.

Preferably the biotinylation domain of the tag comprises the sequence of E. coli BCCP (Biotin Carboxyl Carrier Protein of Acetyl-Coa Carboxylase (ACCB)—Swiss-Prot Database Accession no. P02905), the nucleotide and amino acid sequence of which is:
BCCP Domain:
Nucleotide (SEQ ID NO:1)

```
gcagcagcggaaatcagtggtcacatcgtacgttccccgatggttggtac
tttctaccgcaccccaagcccggacgcaaaagcgttcatcgaagtgggtc
agaaagtcaacgtgggcgatacccctgtgcatcgttgaagccatgaaatg
atgaaccagatcgaagcggacaaatccggtaccgtgaaagcaattctggt
cgaaagtggacaaccggtagaatttgacgagccgctggtcgtcatcga
gtaa
```

Amino Acid: (SEQ ID NO:2)

```
AAAEISGHIVRSPMVGTFYRTPSPDAKAFIEVGQKVNVGDTLCIVEAMKM
MNQIEADKSGTVKAILVESGQPVEFDEPLVVIE-
```

Alternatively, other sequences encoding BCCP known in the art can be used as the biotinylation domain of the invention, for example other BCCP proteins from the Swiss-Prot database:
BCCA_MYCLE (P46392) (SEQ ID NO:19)
 Acetyl-/propionyl-coenzyme A carboxylase alpha chain [Includes: Biotin carboxylase (EC 6.3.4.14); Biotin carboxyl carrier protein (BCCP)]. {GENE: BCCA OR ML07260R B1308_C1_129}—*Mycobacterium leprae*
BCCA_MYCTU (P46401) (SEQ ID NO:20)
 Acetyl-/propionyl-coenzyme A carboxylase alpha chain [Includes: Biotin carboxylase (EC 6.3.4.14); Biotin carboxyl carrier protein (BCCP)]. {GENE: ACCA1 OR BCCA OR RV2501C OR MT25760R MTCY07A7.07C}—*Mycobacterium tuberculosis*
BCCP_ANASP (Q06881) (SEQ ID NO:21)
 Biotin carboxyl carrier protein of acetyl-CoA carboxylase (BCCP). {GENE: ACCB}—*Anabaena* sp. (strain PCC 7120)
BCCP_ARATH (Q42533) (SEQ ID NO:22)
 Biotin carboxyl carrier protein of acetyl-CoA carboxylase, chloroplast precursor (BCCP). {GENE: CAC1 OR BCCP1 OR AT5G16390 OR MQK4.12}—*Arabidopsis thaliana* (Mouse-ear cress)
BCCP_BACSU (P49786) (SEQ ID NO:23)
 Biotin carboxyl carrier protein of acetyl-CoA carboxylase (BCCP). {GENE: ACCB OR FABE}—*Bacillus subtilis*
BCCP_CHLMU (Q9PKR5) (SEQ ID NO:24)
 Biotin carboxyl carrier protein of acetyl-CoA carboxylase (BCCP). {GENE: ACCB OR TC0399}—*Chlamydia muridarum*
BCCP_CHLPN (Q9Z901) (SEQ ID NO:25)
 Biotin carboxyl carrier protein of acetyl-CoA carboxylase (BCCP). {GENE: ACCB OR CPN01830R CP0585}—*Chlamydia pneumoniae* (*Chlamydophila pneumoniae*)
BCCP_CHLTR (O84125) (SEQ ID NO:26)
 Biotin carboxyl carrier protein of acetyl-CoA carboxylase (BCCP). {GENE: ACCB or CT123}—*Chlamydia trachomatis*
BCCP_CYACA (O19918) (SEQ ID NO:27)
 Biotin carboxyl carrier protein of acetyl-CoA carboxylase (BCCP). {GENE: ACCB}—*Cyanidium caldarium* [Chloroplast]
BCCP_ECOLI (P02905) (SEQ ID NO:28)
 Biotin carboxyl carrier protein of acetyl-CoA carboxylase (BCCP). {GENE: ACCB OR FABE OR B3255 OR Z4615 OR ECS4127}—*Escherichia coli, Escherichia coli* O157:H7
BCCP_HAEIN (P43874) (SEQ ID NO:29)
 Biotin carboxyl carrier protein of acetyl-CoA carboxylase (BCCP). {GENE: ACCB OR FABE OR HI0971}—*Haemophilus influenzae*
BCCP_LYCES (P05115) (SEQ ID NO:30)
 Biotin carboxyl carrier protein of acetyl-CoA carboxylase (BCCP) (Fragment).—*Lycopersicon esculentum* (Tomato)
BCCP_PORPU (P51283) (SEQ ID NO:31)
 Biotin carboxyl carrier protein of acetyl-CoA carboxylase (BCCP). {GENE: ACCB}—*Porphyra purpurea* [Chloroplast]
BCCP_PROFR (P02904) (SEQ ID NO:32)
 Biotin carboxyl carrier protein of methylmalonyl-CoA carboxyl-transferase (Transcarboxylase, 1.3S subunit).—*Propionibacterium freudenreichii shermanii*
BCCP_PSEAE (P37799) (SEQ ID NO:33)
 Biotin carboxyl carrier protein of acetyl-CoA carboxylase (BCCP). {GENE: ACCB OR FABE OR PA4847}—*Pseudomonas aeruginosa*
BCCP_SOYBN (Q42783) (SEQ ID NO:34)
 Biotin carboxyl carrier protein of acetyl-CoA carboxylase, chloroplast precursor (BCCP). {GENE: ACCB-1}—*Glycine max* (Soybean)
BCCP_STRMU (P29337) (SEQ ID NO:35)
 Biotin carboxyl carrier protein (BCCP).—*Streptococcus mutans*

Also included within the scope of the invention are biotinylation domains encoded by or comprising artificial sequences, for example where one or more amino acids have been altered by conservative substitution. Such sequences can be rationally designed or derived from the sequences of BCCP given above, by methods known in the art. It is essential that these sequences have a secondary and tertiary structure that permits the artificial sequence to be recognised and biotinylated by a biotin ligase enzyme.

In a second aspect, the invention provides the use of a tag moiety comprising a biotinylation domain for determining the folded state of a protein of interest by attachment of said tag moiety to the N-terminus or C-terminus of said protein of interest.

In this second aspect, the tag moiety comprising a biotinylation domain as defined herein is a protein or protein domain which is conditionally biotinylated by a biotinylating enzyme, for example biotin ligase expressed in the host cell in which expression takes place or exogenously applied biotin ligase, for example, used to biotinylate proteins in a cell-free extract. Essentially, the domain can only be biotinylated through recognition of the folded structure of the domain by the enzyme such that the domain in linear, mis-folded or aggregated, form for example in inclusion bodies, is not biotinylated. The folding of the tag and its subsequent biotinylation is dependent on the correct folding of the protein N-terminal to the C-terminal tag and vice versa.

In a third aspect the invention provides a method of increasing the solubility of a protein of interest when expressed in a host cell comprising the steps of:
a) attaching a first nucleic acid molecule encoding a tag moiety comprising a biotinylation domain to a second nucleic acid molecule encoding said protein of interest to form a construct such that the tag moiety in the expressed product of the combined first and second nucleic acid molecules comprises said tag moiety located at the N-terminus or C-terminus of said protein of interest
b) expressing said construct in a host cell In a fourth aspect the invention provides a method of determining the folded state of a protein of interest comprising the steps of:
a) attaching a first nucleic acid molecule encoding a tag moiety comprising a biotinylation domain to a second nucleic acid molecule encoding said protein of interest to form a construct such that the tag moiety in the expressed product of the combined first and second nucleic acid molecules comprises is located at the N-terminus or C-terminus of said protein of interest
b) expressing said construct in a host cell under conditions such that only a correctly folded biotinylation domain present in said tag moiety is ligated with biotin
c) determining the folded state of the protein of interest comprising said tag moiety by the presence or absence of a biotin group in the protein expressed from said construct The uses of the first and second aspect of the invention and the methods of the third and fourth aspects of the invention are preferably carried out in a multiplexed manner on more than one protein of interest. For example, wherein the protein of interest is encoded by nucleic acid molecule which forms part of a library comprising two or more different coding sequences and, optionally, wherein the different coding sequences are modified to contain the tag moiety and expressed in parallel.

Thus in a fifth aspect the invention provides a library of nucleic acid molecules encoding proteins of interest wherein each coding sequence is modified to incorporate at the N-terminus or C-terminus of the encoded protein a tag moiety comprising a biotinylation domain. Such libraries may be generated using known techniques in the art. Usefully, the library can be generated using the COVET methodology described in WO 01/57198.

Accordingly, in a sixth aspect, the invention provides a library of proteins produced from the methods of the third and fourth aspects of the invention or expressed from the library of the fifth aspect of the invention. Such libraries may be arrayed on a solid substrate, for example through immobilisation to that substrate via, for example, a streptavidin-biotin link via the BCCP tag present on the proteins of the library.

The Inventors have also determined that the addition of DNA encoding a BCCP tag 5' to and in-frame with genes of interest in a library has the effect of significantly increasing the number of encoded proteins of interest which are expressed from that library compared to a library encoding the same proteins, but lacking the BCCP tag encoding sequence. Such relative expression differences between "tagged" and "un-tagged" libraries can be detected or measured qualitatively, for example using western blotting techniques as known in the art.

Thus, in a seventh aspect, the invention provides the use of a nucleic acid molecule encoding a tag moiety comprising a biotinylation domain for increasing the proportion of clones in a library that express the protein of interest encoded by each of said clones at detectable levels, for example as measured by conventional western blotting, by attachment of said nucleic acid molecule encoding said tag 5' to and in-frame with the gene encoding said protein of interest in each of said clones.

Accordingly in an eighth aspect, the invention provides a method of increasing the proportion of clones in a library that express the protein of interest encoded by each of said clones in a host cell at detectable levels, comprising the steps of:
a) attaching a first nucleic acid molecule encoding a tag moiety comprising a biotinylation domain 5' to and in-frame with a second nucleic acid molecule encoding said protein of interest in a clonal member of said library to form a construct such that the tag moiety in the expressed product of the combined first and second nucleic acid molecules comprises said tag moiety located at the N-terminus of said protein of interest
b) expressing said construct in a host cell Preferred features of each aspect of the invention are as defined for each other aspect, *mutatis mutandis*.

Whilst the tags, methods and libraries of the invention are particularly suited to facilitating parallel expression and purification/immobilisation of proteins encoded by a library of sequences (by a common method of solublisation and purification of the proteins of interest), the invention can also be applied to other methodologies known in the art. For example, an N-terminal or C-terminal tag according to the invention (for example BCCP) can be used to increase both protein expression and solubility in:
Vaccine production
Therapeutic protein production
Antigen production used for the generation of monoclonal or polyclonal antibodies, monoclonal antibody or single chain antibody production
Enzyme production
Drug target discovery by mapping cellular protein-protein interactions "the interactome"
Drug target validation by generation of protein drug targets including, but not exclusively, kinases, phosphatases, cell receptors or proteases for screening, enzyme and/or toxicology studies and any other biochemical analysis.

The invention will now be further described by the following non-limiting examples which refer to the accompanying figures in which:

FIG. 1 shows the colony western data using Streptavidin-HRP conjugate as the probe. The clones expressing in-frame GFP-BCCP that fluoresced green are also biotinylated. The bottom row are clones that harbour pMSC301 (no bccp gene sequence in the plasmid), and signal obtained is the background signal of endogenous biotinylated AccB. The second row from the bottom are the clones harbouring pMSC302

(overexpressing accB). The other negative clones (out of frame fusions or vector religated did not fluoresce green and were not biotinylated).

FIG. 2 shows colony western data using Streptavidin-HRP conjugate as the probe. The clones expressing in-frame GST-GFP-BCCP that fluoresced green are also biotinylated. Also shown as biotinylation positive signal is the protein GST-BCCP. The negative control is clones that harbour pMSC301 (no bccp gene sequence in the plasmid), and signal obtained is the background signal of endogenous biotinylated AccB. The positive control is the clone harbouring pMSC302 (overexpressing accB). The other negative clones (out of frame fusions or vector religated did not fluoresce green and were not biotinylated).

FIG. 3 shows western blot analysis of the protein extract from cells expressing GFP-BCCP. The signal obtained at approximately 37 kDa., is the expected Mr of GFP-BCCP. Another signal seen at 18 kDa is that of endogenous biotinylated AccB protein, also seen in the GFP-BCCP negative lanes. As expected, the 18 kDa. signal is stronger, when no recombinant biotinylated protein is expressed.

Lanes 1, 2 and 3: Protein extract from clones harbouring pGFP-BCCP, expressing intact GFP-BCCP protein.

Lanes 4, 5 and 6: Protein extract from clones harbouring pMSC301A, B, and C respectively, used as negative control in the experiment.

FIG. 4 shows western blot analysis of protein extracts from cells expressing GST-GFP-BCCP, and GST-BCCP. Biotinylated proteins of expected Mr. are observed (63 kDa for GST-GFP-BCCP and 37 kDa for GST-BCCP). In all the lanes 18 kDa signal for endogenous AccB is present.

Lanes 1, 2 and 4 are protein extract from cells expressing GST-GFP-BCCP.

Lane 3 is the protein extract from cells expressing GFP-BCCP as a positive control in this expt.

Lanes 5 and 6: Protein extract from clones harbouring pMSC301A, and B as negative controls in the blot.

Lanes 7 and 8: Protein extracts from cells expressing GST-BCCP.

FIG. 5 shows a colony western blot using streptavidin-HRP as the probe for biotinylation of BCCP in the fusion protein. All clones that were marked to be fluorescing green when excited at 365 nm wavelength, were also biotinylated (positive signal above the background). The intensities of positive signals varies as does the green phenotype. Increased sensitivity of detection using streptavidin-HRP conjugate, picked up few additional clones.

FIG. 6 shows protein expression results of the human gene set cloned into the Avi-Tag vector pQE82L-GFP-biotin. Single ampicillin resistant colonies were used to inoculate 1 ml of LB media containing 100 µg/ml ampicillin (LB-Amp) and grown over-night at 37° C. with shaking. The next day a 1:100 dilution was made into fresh LB-Amp and cells grown at 37° C. until OD600=0.6 to 1.0. IPTG was then added to a final concentration of 1 mM and growth continued at 30° C. for 4 hours. 10 µl of cell culture was then taken and analysed by 4-20% SDS-PAGE Western blot and probed with HRP-conjugated streptavidin. Numbers labeled for each lane refer to the B# in Table 1. The molecular weight markers are: aprotin (7.6 kDa), lysozyme (18.4 kDa), soybean trysin inhibitor (32.5 kda), carbonic anhydrase (45.7 kDa), BSA (78 kDa), B-galactosidase (132 kDa) and myosin (216 kDa).

FIG. 7 shows protein expression results of the human gene set cloned into the BCCP expressing vector pMD004. Single ampicillin resistant colonies were used to inoculate 1 ml of LB media containing 100 µg/ml ampicillin (LB-Amp) and grown over-night at 37° C. with shaking. The next day a 1:100 dilution was made into fresh LB-Amp and cells grown at 37° C. until OD600=0.6 to 1.0. IPTG was then added to a final concentration of 1 mM and growth continued at 30° C. for 4 hours. 10 µl of cell culture was then taken and analysed by 4-20% SDS-PAGE Western blot and probed with HRP-conjugated streptavidin. Numbers labeled for each lane refer to the B# in Tables 1 and 2. The molecular weight markers are: aprotin (7.6 kDa), lysozyme (18.4 kDa), soybean trysin inhibitor (32.5 kDa), carbonic anhydrase (45.7 kDa), BSA (78 kDa), B-galactosidase (132 kDa) and myosin (216 kDa).

FIG. 10 (SEQ ID NO: 3) shows the cloning site of plasmid pIFM101A

FIG. 11 (SEQ ID NO: 4) shows the cloning site of plasmid pIFM101B

FIG. 12 (SEQ ID NO: 5) shows the cloning site of plasmid pIFM101C

EXAMPLES

Example 1

Figure 1:
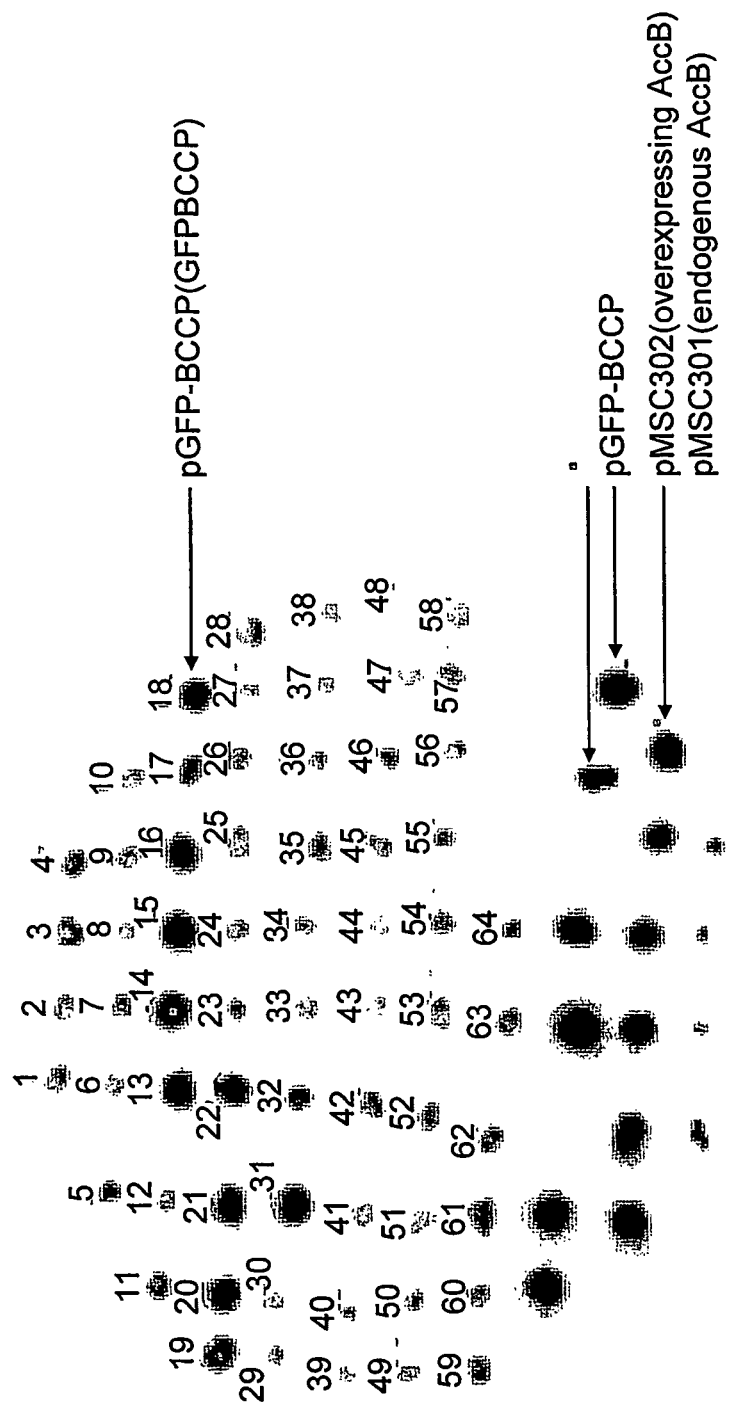

Use of BCCP as a Protein Folding Marker

Methods

1. Isolation of Biotin Carboxyl Carrier Protein (C-terminal Domain of Acetyl-CoA Carboxylase) from *E. coli* K 12 Strain The DNA sequence encoding the entire coding region of acetyl-CoA carboxylase was amplified by PCR from genomic DNA of XL1-Blue (Stratagene) cells, using the following gene specific primers.

accbfor1: 5' GAT GGATCCGATATTCGTAAGATTAAAAAACTGATCG 3' (SEQ ID NO:6) with BamHI site at the 5' end.

bccprev1: 5' GATGAGCTCAAGCTTTTACTCGATGACGACCAGCGGCTCGTC 3' (SEQ ID NO:7) containing SacI and HindIII site.

The PCR amplification was carried out using Pwo polymerase (Roche) using standard cycling conditions (94° C. 5 min; 94° C. 30 sec; 64° C. 1 min; 72° C. 1 min; 30 cycles; 72° C. 5 min).

The PCR amplified gene sequence was cloned into the BamHI and SacI site of the *E. coli* expression vector pQE-80 (Qiagen) inframe with the N-terminus hexahistidine tag to form the plasmid pMSC302. The identity of the gene sequence was confirmed by restriction mapping and DNA sequencing. The DNA sequence corresponding to the C-terminal domain of AccB known as biotin carboxyl carrier protein (BCCP) was amplified by PCR using the same reverse primer as above and a new forward primer.

bccpfor1: 5'GATCTGCAGGGCTCCGCAGCAGCGG-AAATCAGTGGTCACATCG 3' (SEQ ID NO:8) containing PstI site for cloning and two extra codons for glycine and serine.

2. Construction of Vectors:

The vector pQE-80 was redesigned to delete the DNA sequence for hexahistidine tag, add additional cloning sites (NotI and SfiI), and have three different reading frames from the start ATG (pMSC301A/B/C). This was carried out by inverse PCR using the primer sets; pQErev1: 5'P CATAGT-TAATTTCTCCTCTTTAATGAATTCTG 3' (SEQ ID NO:9); pQEfwd1: 5' GCGGCCGCGGCCATTACGGCCGGATCC-GCATGCGAGCTCGG TACCCCC 3' (SEQ ID NO:10); pQEfwd2: 5' G+pQEfwd1; pQEfwd3: 5' GC+pQEfwd1 for A, B, and C reading frames respectively. The PCR was carried out using Pwo polymerase (94° C. 2 min; 94° C. 30 sec; 63.5° C. 1 min; 72° C. 6 min; 25 cycles; 72° C. 10 min).

The bccp gene sequence was cloned into the PstI-HindIII sites of pMSC301 A, B, and C vectors to generate pMSC301A,B,C/BCCP.

The DNA sequence encoding GFPuv (Clontech) was amplified by PCR using the primer set pQEGFPfor1: 5' GGGCCGGTGGCAGCGCGAGTAAAGGAG AAGA ACTTTTCACTGG 3' (SEQ ID NO:11) (with SmaI half site and a linker region) and pQEGFPrev1: 5' GAT CTGCAGGGTACCGGATCCTTTGTAGAGCTCATCC-ATGCC 3' (SEQ ID NO:12) (with PstI, Kpn I and Bam HI sites). The PCR amplified product was cloned into the SmaI-PstI sites of pMSC301A, B and C/BCCP in-frame to DNA sequence encoding the N-terminus of BCCP (GFP-BCCP) to generate the vectors pMSC303A, B, and C.

The plasmid construct pMSC303B was restricted with NotI, the staggered ends were made blunt using the filling in reaction of T4 Polymerase (NEB), restricted with Sma I and religated (plasmid designated as pGFP-BCCP).

The vectors pMSC301A/BCCP and pMSC303A were restricted with NotI, the overhangs blunted using T4 DNA polymerase, restricted with SmaI and were used to clone the DNA fragment encoding GST forming the plasmid constructs pGST-BCCP and pGST-GFP-BCCP respectively. The DNA sequence encoding GST was amplified by PCR using the primers; GSTfwd01: 5' TCCCCTATACTAGGTTATTGG 3' (SEQ ID NO:13) and GSTrevexoN: 5' GGGCGTCACGA TGAATTCCCGGG 3' (SEQ ID NO:14) and pGEX-2T (Pharmacia) as template.

The NotI and SfiI cloning sites of the vectors pMSC303A,B and C were replaced by the SfiI overhang compatible restriction site, DraIII to generate the vectors pIFM101A, B, and C. This was carried out by inverse PCR using the primers; DrafwdA: 5' CACTTAGTGGGATCCG-CATGCGAGCTCGGTACCCC 3' (SEQ ID NO:15); DrafwdB: 5' G+DrafwdA; DrafwdC: GA+DrafwdA. The reverse primer used was pQErev1 as described earlier. The PCR conditions used were same as before.

A set of nested deletions recessed at 3' ends of human heart cDNAs (Clontech) were cloned into the DraIII-SmaI sites of the vectors pIFM101A, B, and C to form the plasmid pX-GFP-BCCP.

The correct DNA sequence of all the constructs used in the study were confirmed by sequencing.

3. Generation of Nested Deletions (Recessed at 3' Ends) of Human Heart cDNAs

The COVET methodology was used to generate the deletion set which is the subject of patent application Nos. GB0020357.0, U.S. Ser. No. 60/247,995 and WO 01/57198. In brief, ~100 ng template plasmid library (human heart cDNA library in pDNR-LIB from Clontech) was amplified by PCR using vector-specific primers SP5forward: 5'ATGCT-CATGAGGCCGGCCGGGAATTC GGCCATTACGGCCGG3' (SEQ ID NO:16) with FseI and SfiI sites, and SP3reverse: 5'GTCTAGAAAGCTTCTC-GAGGGCCG3' (SEQ ID NO:17), to optimally incorporate alpha-phosphothioate dTTPs (α-S-dTTP; Amersham). The PCR reaction was carried out using 50 pmol each primer, 2.5 units thermostable polymerase (lacking a 3' to 5' exonuclease activity e.g. Taq polymerase), a standard buffer and the deoxynucleotide triphosphate mix: 200 μM dATP, 200 μM dGTP, 200 μM dCTP, 100 μM dTTP, 100 μM α-S-dTTP. The PCR amplified products were purified using QIAquick PCR cleanup kits (Qiagen) and subjected to FseI digestion to produce a 3' nucleotide overhang which protects the 5' end of the dsDNA from subsequent hydrolysis by exonuclease III (NEB). Exonuclease III digestion was performed using standard conditions and the presence of phosphothioate internucleotide linkages blocked any further hydrolysis. This generated a nested set of sense strand 3' deletions. Mung bean nuclease (New England Biolabs) was used to remove ssDNA from the antisense strand and therefore blunt the dsDNAs in preparation for directional cloning after further digestion with SfiI. These inserts after size fractionation by agarose gel electrophoresis were cloned into the DraIII and SmaI sites of the vectors pIFM101A, B and C. The ligated products were then used to transform XL1-Blue cells (Stratagene).

4. Expression of the Fusion Proteins

The *E. coli* strains XL1-Blue or XL10-Gold (stratagene) were used as host cells and were transformed (electroporation or chemical method) using various plasmid constructs. The transformation mixture was plated at an appropriate dilution on a nitrocellulose membrane placed on LB-Agar containing 100 μg/ml carbenicillin. After overnight incubation at 30° C. the membranes were transferred onto LB-Agar containing 400 μM IPTG and carbenicillin and incubated for another 4-5 hrs at 30° C. The GFP activity of the clones were assessed by visualizing the clones at 365 nm wavelength of the UV-transilluminator. The membranes were processed for detecting biotinylated BCCP or GFP. For analysing the proteins by western blot the cultures were induced at mid log phase (optical density at 600 nm of 0.5 to 0.6) by adding 400 μM of IPTG to the culture and growth of cells continued for another 3-4 hours at 30° C. At the end of the induction period, cells were harvested, proteins resolved on 10-20% gradient SDS-gel (Invitrogen), blotted onto nitrocellulose membrane and probed with various antibodies or streptavidin.

5. Detection of Biotinylated BCCP

The biotinylation of BCCP was detected by probing with a streptavidin-horseradish peroxidase (HRP) conjugate (Amersham) on colony blots (as described) or on western blots as known in the art.

The clones were either gridded robotically, or the transformation mix was plated, onto nitrocellulose membrane (Amersham) placed on a LB agar plate containing carbenicillin. After overnight incubation at 30° C., the membrane was placed onto a fresh LB agar plate containing carbenicillin and IPTG (400 μM). The plate was incubated for another 4-5 hours at 30° C. The colonies on the membrane were subjected to alkaline lysis and the membrane blocked prior to addition of the probe. The membrane is first placed on two sheets of Whatmann 3 paper pre soaked with 0.5 (M) NaOH, 1.5 (M) NaCl for 10 min. The membrane is neutralised by placing on Whatmann 3 sheets soaked with 1 (M) TrisHCl pH 7.5, 1.5 (M) NaCl for 5 min, two times. The membrane is then transferred onto Whatmann 3 sheets wetted in PBS-T (0.1%) containing 1% SDS for 10 mins. The membrane is then washed thoroughly in PBS-T ensuring that all the cell debris has been dislodged. The blot is then ready to be processed in the same manner as a western blot.

The Streptavidin-HRP conjugate was used at a dilution of 1:4000 and the signal was detected by chemiluminescence using the ECL system from Amersham.

6. Detection of GFP Activity

The green fluorescence of GFP was visualized by exciting the colonies at 365 nm wavelength using a transilluminator.

7. Detection of GST

An anti-GST monoclonal antibody (Sigma) was used as an immunoprobe to detect expression of GST. The antibody was used at a dilution of (1:3000) and the immunoreactive signal was detected using the ECL system from Amersham.

Results
Absolute Correlation of GFP Activity and Biotinylation of BCCP

Figure 2:
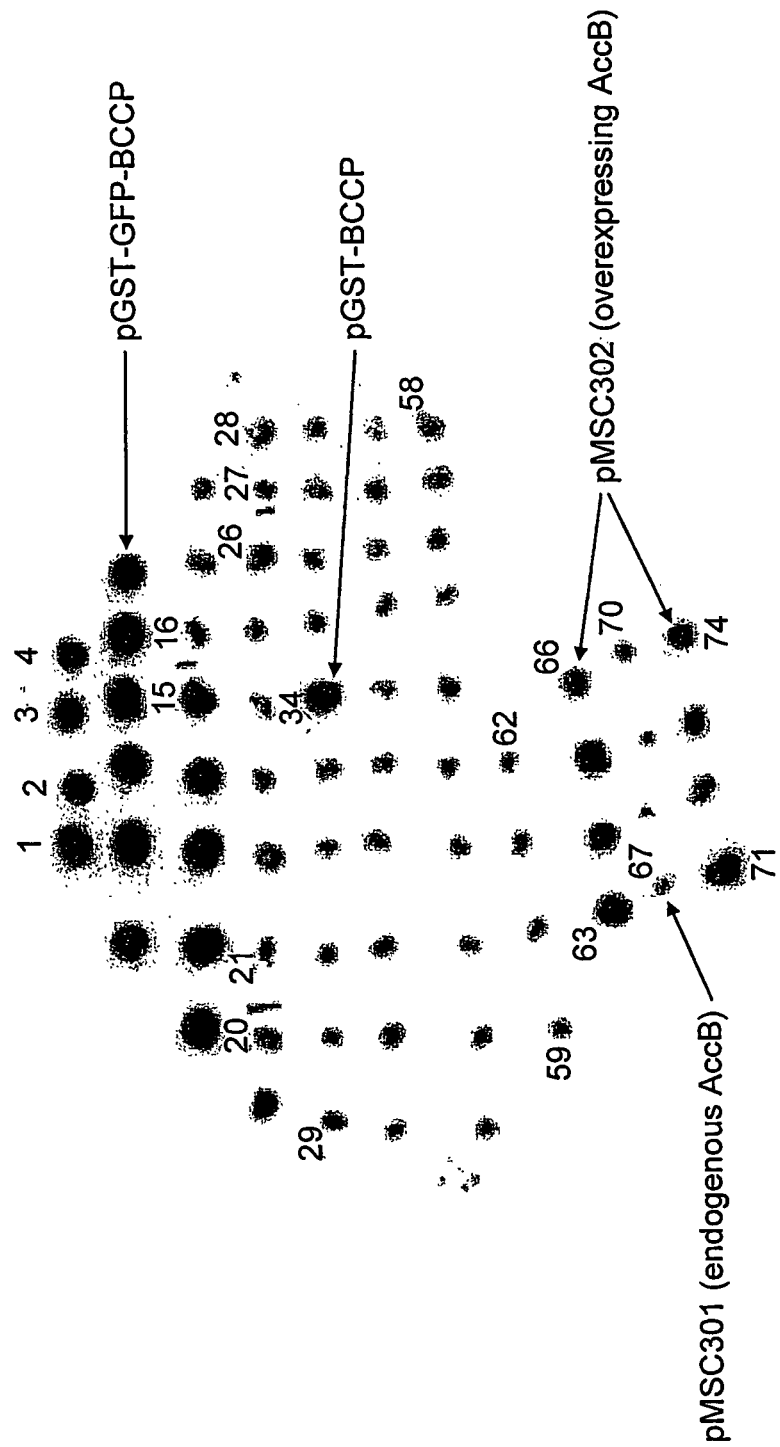
Figure 3:
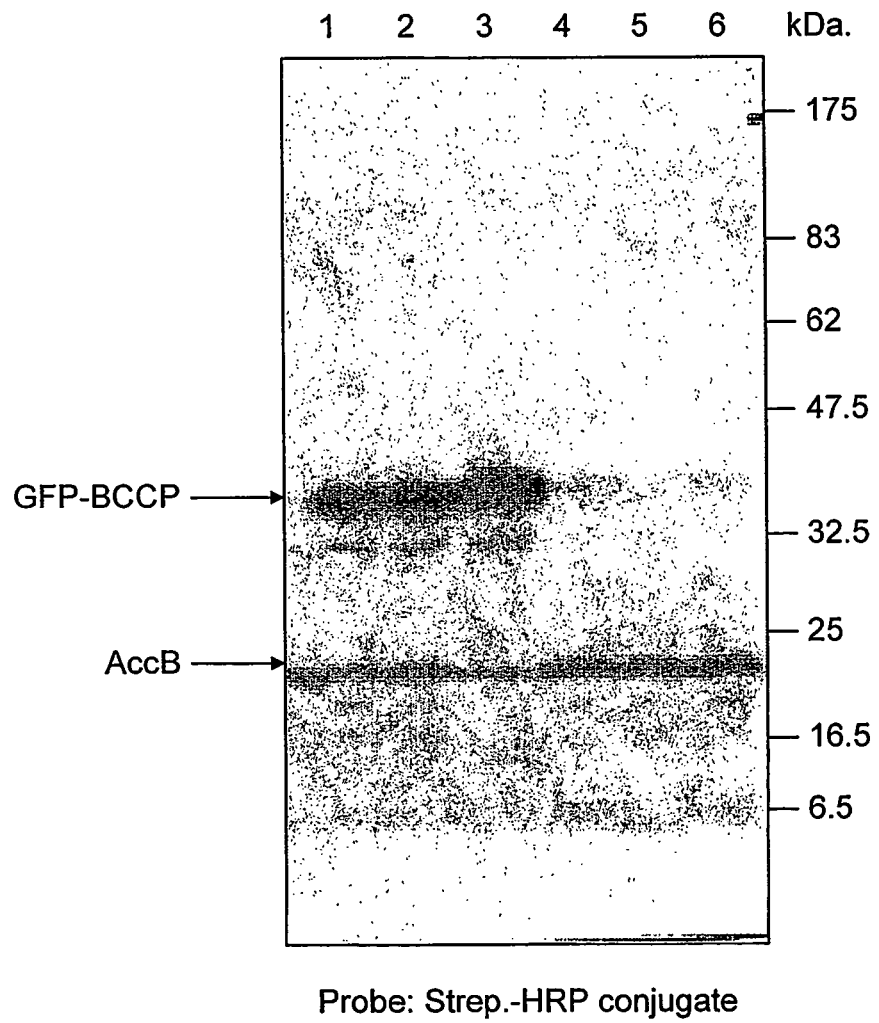
Figure 4:
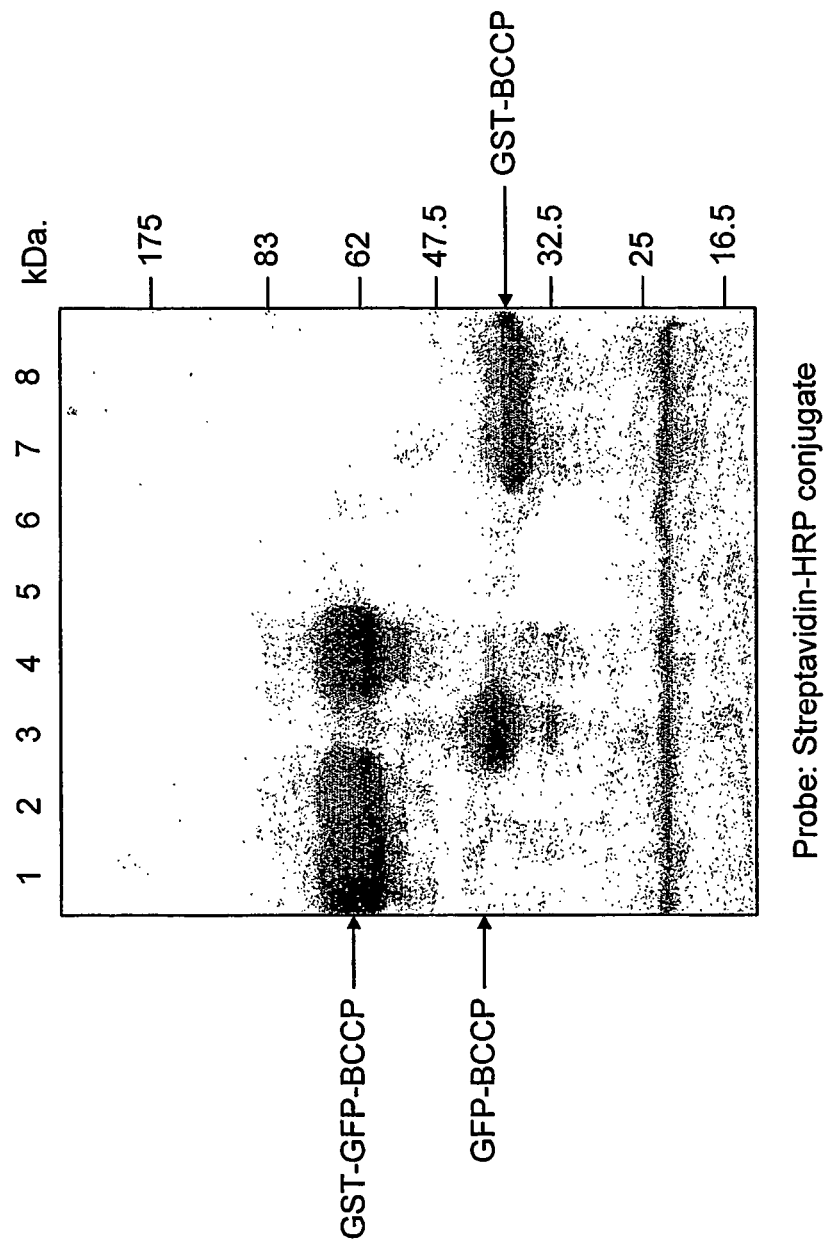

FIGS. 1 and 2 show the colony western data using streptavidin-horseradish peroxidase as the probe. Only the correct in-frame fusion of GST-GFP-BCCP, GST-BCCP and GFP-BCCP gave strong positive signal significantly above the general background from endogenous biotinylated AccB. Out-of-frame fusions resulting from the cloning strategy used, did not give rise to positive signals. All and only biotinylated fusion proteins (GST-GFP-BCCP and GFP-BCCP) fluoresced green when excited at 365 nm. The fluorescence is indicative of correct folding of the fusion protein and this result demonstrated that correctly folded proteins with BCCP as the C-terminal fusion partner is an active substrate for biotin protein ligase (BPL). FIGS. 3 and 4 show that the biotinylated proteins are of expected molecular weight, confirming the proteins as intact and unproteolysed.

A More Comprehensive Study of a Group of Proteins

Figure 5:
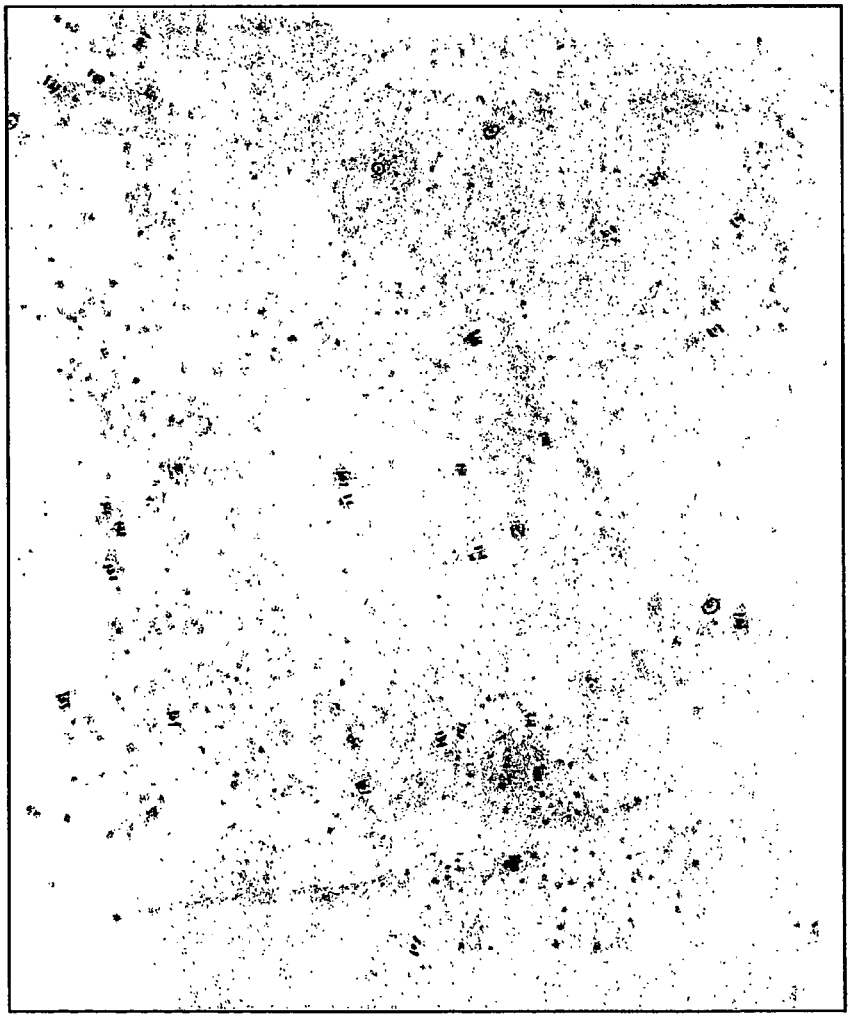

Human heart cDNAs were recessed at 3' ends so as to remove the stop codon of the ORFs using controlled Exonuclease III (NEB) digestion. This 3' nested deletion set was then cloned into the vectors pIFM101A,B and C (see FIGS. 9 to 12). The library of resulting fusions to GFP-BCCP will be either in or out of frame. The in frame fusion proteins when expressed as correctly folded soluble proteins fluoresced green under ultraviolet light at 365 nm (GFP is a visual folding marker) and were also biotinylated. FIG. 5 shows a colony western blot probed with streptavidin-horseradish peroxidase conjugate. The positive hits (significantly above the background) are the ones that were marked as green when visualized 365 nm. Only 4 out of 36 were biotinylated but not green visually. This could be due to the fact that the detection method used for biotinylation of BCCP is much more sensitive than visual detection of green fluorescence.

In this experiment many of the fusion proteins would be in-frame to GFP-BCCP but would not fluoresce green as they do not fold properly and are insoluble. The streptavidin-HRP western blot data with a set of complex fusion proteins (FIG. 5) shows that only when the fusion proteins are correctly folded and soluble, as assessed by green fluorescence of GFP, is the BCCP domain of the fusion protein biotinylated. These observations demonstrate that biotinylation of BCCP in the fusion protein is a folding marker as is the green fluorescence of GFP. Since it is known in the art that GFP is a reliable indicator of correct folding then the results here demonstrate that biotinylation of BCCP is also a reliable indicator of correct folding.

Example 2

Use of BCCP as a Protein Solubility Enhancer

Materials and Methods

Vectors.

The pQE82L-GFP-biotin and pMD004 plasmids (FIG. 8) were constructed by standard techniques (T. Maniatis et al (1989) Molecular Cloning: A Laboratory Manual. Cold Spring Harbor Press) and both consist of a pQE82L vector (Qiagen) backbone, with a RGS-His tag followed by either the "Avi-Tag" sequence or BCCP protein domain respectively, followed by a multi-cloning site. They encode the lacI$^q$ repressor for tight regulation of the T5 promoter, and when cut with SmaI and NotI release either the GFP or p53 stuffer fragments to give the vectors ready for gene cloning inserts with a 5'-phosphorylated, blunt end and a 3'-NotI sticky end.

Gene Insert Production.

Human protein domains were chosen and the corresponding genes were PCR amplified from cDNA libraries. The 5'-phosphorylated forward primers consist of the first 24 bp at the beginning of the relevant sequence, starting with a full codon. Some of the forward primers are longer to incorporate a G or C at the 3' end. The reverse primers consist of the last 24 bp of the relevant sequence (longer if necessary to incorporate a G or C at the 5' end) which is then appended to the beginning of the reverse primer template (TGATAGAAGAGCGGCCGC) (SEQ ID NO:18). The final reverse primer would be the reverse complement of this. This primer results in the stop codon of all the fusions being defined and followed by a NotI site for cloning into the N-terminal tagging vector described above. Two cDNA templates were combined at a final concentration of 10 ng/μl. These were a) human heart cDNA plasmid library (Life Technologies) & b) HeLa cell cDNA plasmid library (Invitrogen). All primers were reconstituted in distilled water to 100 pmols/μl. A master mix was prepared (without primers) from: Template (10 ng), PWO polymerase buffer with magnesium sulphate (1x final concentration), dNTPs (5 mM final conc.), PWO polymerase (2.5 units), dimethyl sulfoxide (10% final conc.) and distilled water to a final volume of 48 μl per reaction. The master mix was aliquoted into 96 well PCR plates (Eppendorf) and 1 μl of each primer added on ice. Conditions were as follows: 94 for 3 mins then 94 for 30 secs, 59 for 30 secs, 72 for 2 mins (32 cycles) and finally 72 for 7 mins. Products were checked on 2% agarose gels/TBE and purified using Qiaquick PCR purification columns (Qiagen). Clean dsDNA was digested with NotI in a standard digestion mixture and cleaned again.

Hoescht 33258 Assay.

To quantify the dsDNA in preparation for cloning a low range standard curve of an unrelated, clean PCR product in 1:1000 Hoescht dye (stock 1 mg/ml)/1xTNE (Tris 10 mM, EDTA 1 mM, NaCl 0.2 M pH 7.4) was set up at 80, 40, 20, 10, 5, 2.5, 1.25, 0 ng/100 μl. 1 μl of each experimental PCR product was added to 99 μl of 1:1000 Hoescht TNE, mixed in clear bottomed, black sided 96 well microtiter plates (Corning) and fluorescence read at 365/465 nm. The standard curve was plotted and dsDNA content of each 'insert preparation' calculated as ng/μl Cloning the Inserts into pOE82L-GFP-Biotin or pMD004.

Inserts were ligated to the vector prep with an approximate molar ratio of 3:1 (insert:vector). Ligations were carried out in a 96-well PCR plate with the rapid DNA ligation kit (Roche). The ligations (2 μl of each) were used to transform 30 μl of XL1-Gold Supercompetent cells (Stratagene), according to the protocol, in a thin wall 96-well PCR plate. After heat shock, the transformations were added to 300 μl of pre-warmed SOC medium in a 96-well deep well block and shaken at 37° C. for 45 minutes. 200 μl of each was plated and incubated at 37° C. overnight. Approximately 0.02 pmoles of vector was used for each ligation. Ampicillin resistant clones were analysed by colony PCR to check for correct insert size and positive clones taken forward for expression screening.

Protein Expression.

Single ampicillin resistant colonies were used to inoculate 1 ml of LB media containing 100 μg/ml ampicillin (LB-Amp) and grown over-night at 37° C. with shaking. The next day a 1:100 dilution was made into fresh LB-Amp and cells grown at 37° C. until OD600=0.6 to 1.0. IPTG was then added to a final concentration of 1 mM and growth continued at 30° C. for 4 hours. 10 μl of cell culture was then taken and analysed by 4-20% SDS-PAGE Western blot as described and probed with HRP-conjugated streptavidin.

Results and Discussion

Figure 6:
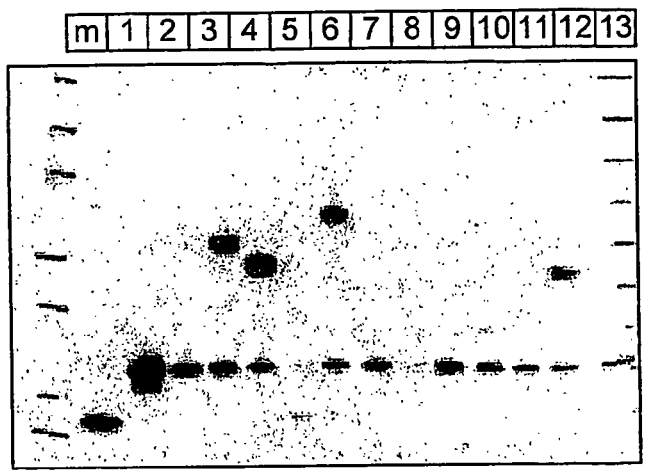
Figure 6:
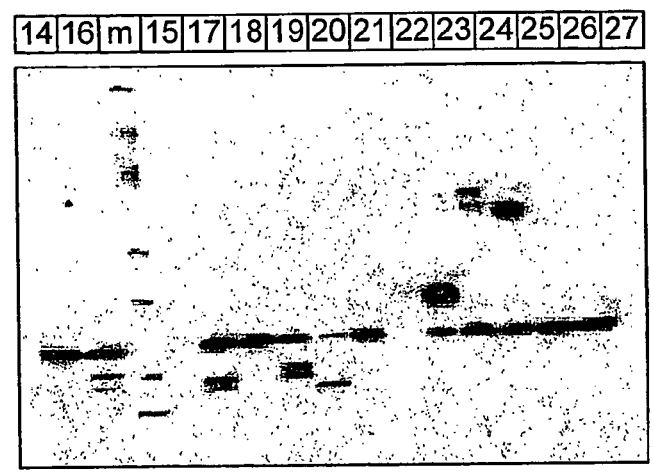
Figure 6:
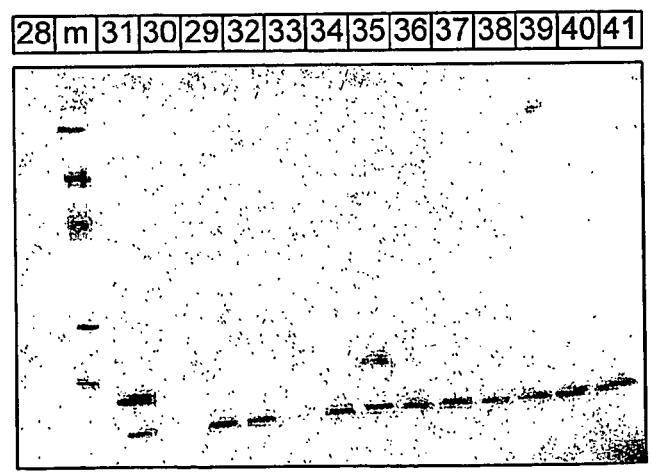
Figure 6:
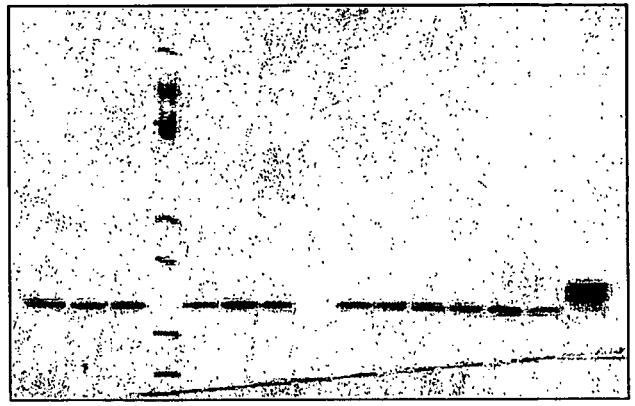
Figure 6:
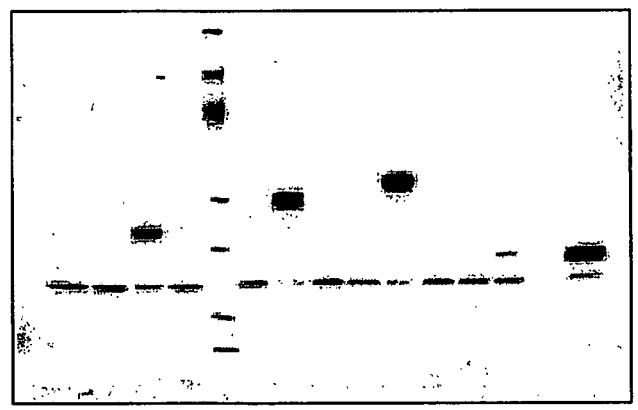
Figure 6:
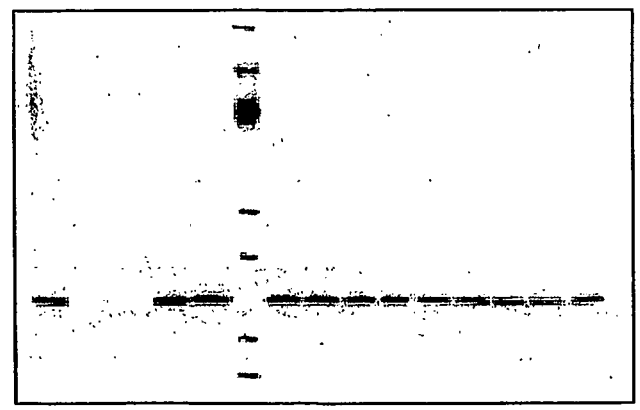
Figure 6:
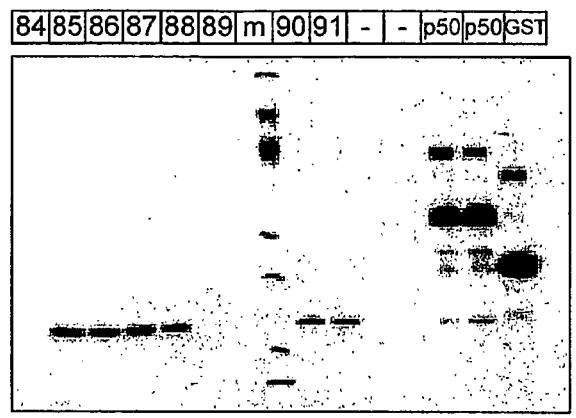
Figure 7:
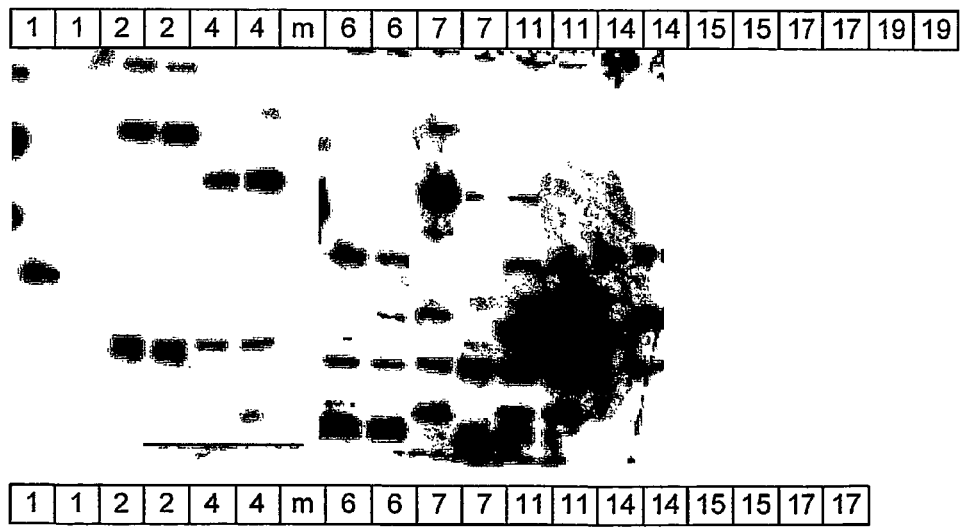
Figure 8:
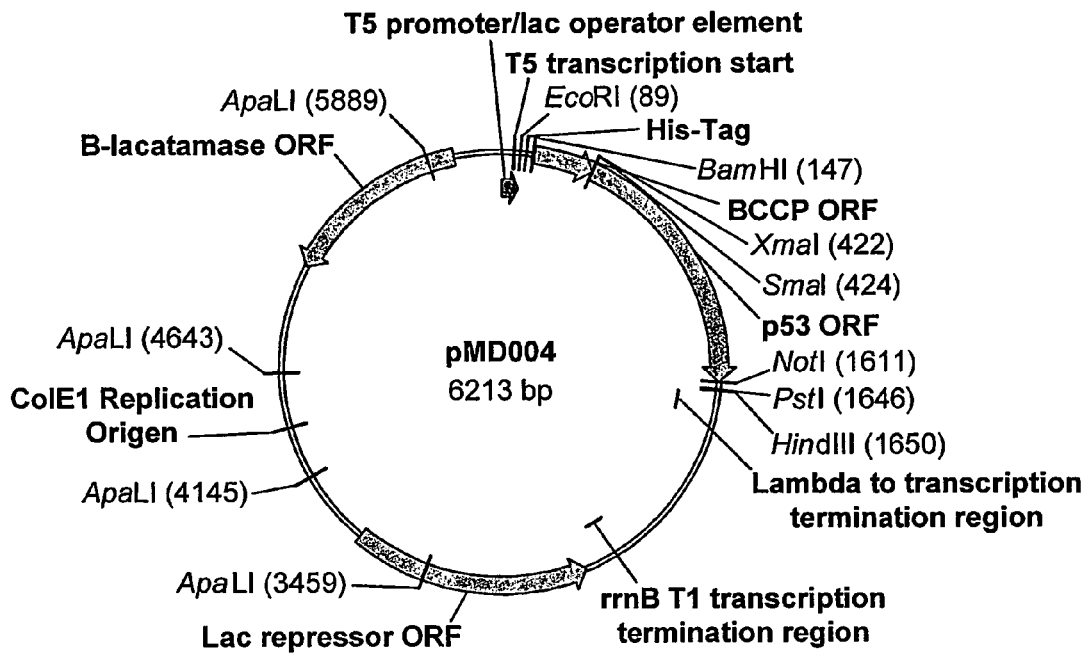
FIG. 8 shows plasmid maps of pMD002 and pMD004.
Figure 8:
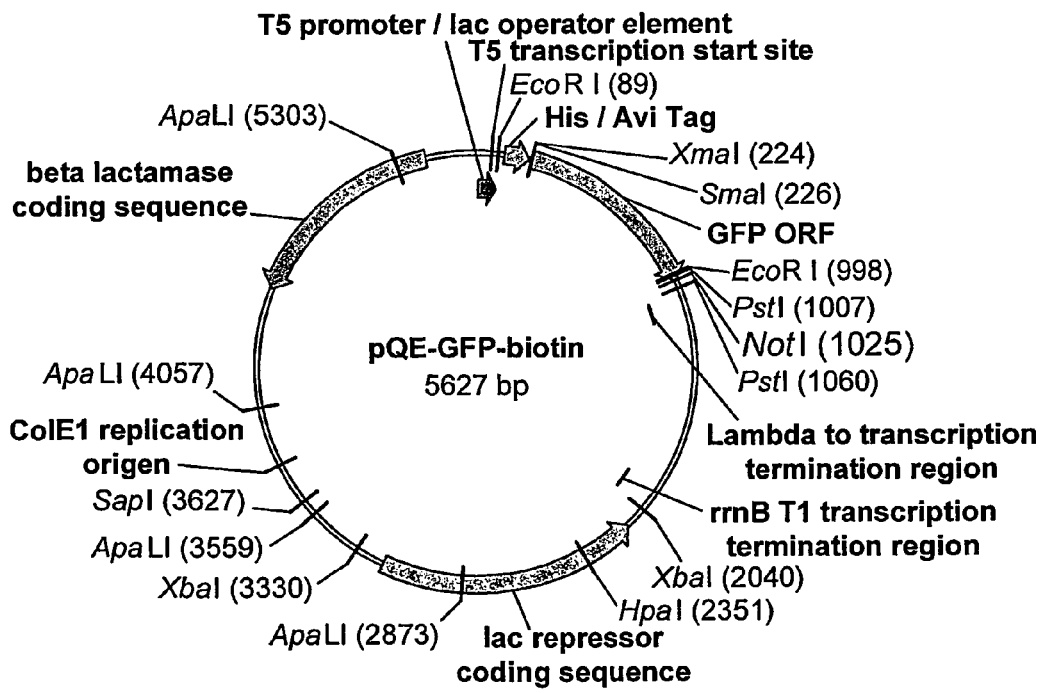
Figure 9:
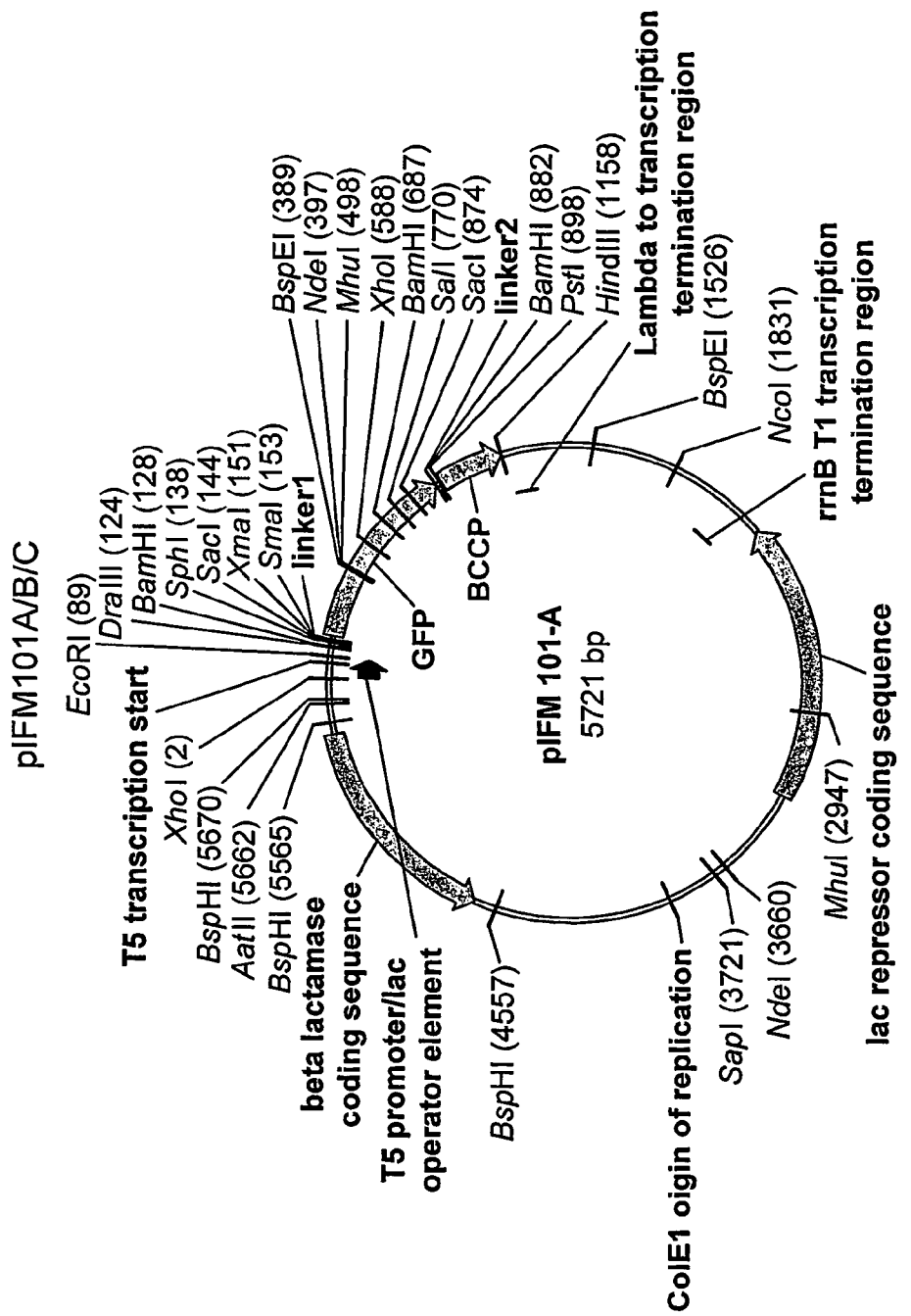
FIG. 9 shows a plasmid map of pIFM101A/B/C

To prove that the BCCP domain can aid protein folding, a defined set of 49 human proteins were cloned into the Sma I/Not I sites of two different vectors: pQE82L-GFP-biotin or pMD004 (FIG. 8). Protein expression from these constructs resulted in proteins being expressed with either a short (19 aa) N-terminal peptide tag (consisting of a hexa-histidine sequence followed by the "Avi-Tag" sequence (U.S. Pat. No. 5,932,433) for pQE82L-GFP-biotin or as fusions to the C-terminus of the *E. coli* BCCP protein (pMD004). A significantly higher success rate for the production of soluble protein was observed when the proteins were expressed as fusions with the BCCP protein (see FIGS. 6 and 7), as summarized in Table 1. For example when fused to the BCCP domain 98% of proteins were expressed solubly compared with when expressed in the absence of the BCCP domain only 48% of clones gave observable expression of which 81% were soluble. The observation that a greater overall number of clones expressed from the pMD004 vector compared with the expression from the pQE82L-GFP-biotin in unlikely to be explained by the "N-end rule" where the amino acids at the N-terminus can be crucial in determining targeting to the proteosome for degradation (Rao H, Uhlmann F, Nasmyth K, Varshavsky A. (2001) *Nature*, 410, 955-9), since in both constructs the N-terminal 12 amino acids are identical. More likely an explanation is that the constructs expressed with an-N-terminal BCCP domain aid protein folding of the downstream proteins, preventing the targeting of the mis-folded proteins to the proteosome. This is also supported by the observation that more proteins expressed in a soluble manner when expressed downstream of BCCP compared with expression from the pQE82L-GFP-biotin vector. The mechanism by which BCCP aids the folding of down-stream protein domains could be either by recruitment of chaperones or by increasing the overall solubility of the fusion protein.

The results presented here strongly indicate that the BCCP domain can increase the overall number of clones expressing soluble protein when expressed as an N-terminal fusion to the target protein. In addition the result indicate that the BCCP domain can increase the solubility of a protein of interest. The tight correlation observed between biotinylation and solubility of expressed fusions demonstrates that biotinylation of BCCP acts as a folding marker when fused to the N-terminus of a protein of interest. In addition, the ability of the BCCP protein to be biotinylated provides a highly specific means to capture the protein on a streptavidin surface.

Table 1. Protein Expression Summary.

Proteins were chosen and corresponding gene inserts were cloned into the pQE-GFP-biotin (vector 1) or the BCCP pMD004 (vector 2) resulting in fusions to the C-terminus of either a hexa-histidine-Avi-Tag peptide or a hexa-histidine-BCCP protein. Only inserts cloned into both vectors are compared in terms of protein expression. Key to table: [1]Internal coding number. [2]Protein database accession number. [3]DNA gene length in base-pairs. [4]. Protein size when expressed as a fusion with BCCP in amino acids (aa). [5]. Protein size when expressed as a fusion with BCCP in kilodalton (kda). [6]Region of ORF cloned (aa). C—cloned but no expression; H—expressing hexa-histidine positive protein in a SDS-PAGE Western blot; B—expressing biotin positive protein in a SDS-PAGE Western blot; S—expressing soluble protein.

TABLE 1

| Gene | B #[1] | PDB[2] | Insert Length bp[3] | Fusion aa[4] | Fusion Kda[5] | Part Cloned[6] | Expression Vector 1 | Expression Vector 2 |
|---|---|---|---|---|---|---|---|---|
| Ac.Flb. Gr. Factor | 1 | 2AXM | 408 | 241 | 31.3 | 1-136/136 orf | C.H.B.S. | C.H.B.S. |
| Alc. Dehyd. | 2 | 1DEH | 1143 | 486 | 63.2 | 1-370/374 orf | C. | C.H.B.S. |
| Ad. Kinase | 3 | 1BX4 | 1044 | 453 | 58.9 | 22-362/362 orf | C.H.B.S. | C.H.B.S. |
| Ald. Red | 4 | 1AZ1 | 960 | 425 | 55.3 | 2-315/315 orf | C.H.B.S. | C.H.B.S. |
| Bar-to-Autoint. | 5 | 2EZZ | 285 | 200 | 26.0 | 1-89/89 orf | C.H.B.S. | C.H.B.S. |
| Bleo. Hyd. | 6 | 1CB5 | 1380 | 565 | 73.5 | 1-454/455 orf | C.H.B.S. | C.H.B.S. |
| Bone Morph. P2 | 7 | 3BMP | 198 | 171 | 22.2 | 291-396/396orf | C.H.B.S. | C.H.B.S. |
| Carb. Anhyd. II | 9 | 1A42 | 798 | 371 | 48.2 | 371/371 orf | C. | C.H.B.S. |
| Cyclin-dep Kin 2 | 11 | 1F5Q | 912 | 409 | 53.2 | 1-298/298orf | C.H.B.S. | C.H.B.S. |
| C-Raf1 | 12 | 1GUA | 246 | 187 | 24.3 | 56-131/648orf | C.H. | C.H.B.S. |
| 3-Meth. DNA Glyc. | 14 | 1BNK | 663 | 326 | 42.4 | 80-294/298orf | C. | C.H.B.S. |
| DNA Pase β | 15 | 1BPX | 1010 | 442 | 57.4 | 4-334/334orf | C.H. | C.H.B.S. |
| Gr. F. Rec-bid. P2 | 17 | 1CJ1 | 306 | 207 | 26.9 | 57-152/217orf | C.H.B.S. | C.H.B.S. |
| Hck Kinase | 19 | 3HCK | 336 | 217 | 28.2 | 140-245/526orf | C.H.B.S. | C.H.B.S. |
| C-Jun Proto-Onc | 20 | 1FOSJ | 189 | 168 | 21.8 | 255-322/340orf | C.H.B.S. | C.H.B.S. |
| Urac.-DNA Glyc. | 21 | 4SKN | 678 | 331 | 43.0 | 85-304/304orf | C. | C. |
| Quin. Red. | 22 | 2QR2 | 711 | 342 | 44.5 | 1-230/230orf | C. | C.H.B.S. |
| GSTP1 | 23 | 9GSS | 652 | 322 | 41.9 | 1-209/209orf | C. | C.H.B. |
| Orn. Aminotr. | 25 | 2CAN | 1224 | 513 | 66.7 | 238-439/439orf | C.H.B.S. | C.H.B.S. |
| Angiogenin | 26 | 1AWZ | 369 | 228 | 29.6 | 25-147/147orf | C. | C.H.B.S. |
| Prot. Disulf. Isom. | 28 | 1MEK | 378 | 231 | 30.0 | 18-137/508orf | C. | C.H.B.S. |
| Glyc-Inh. Factor | 29 | 1GIF | 363 | 226 | 29.4 | 1-114/114orf | C.H.B.S. | C.H.B.S. |
| Fk506-Bind. Prot | 30 | 1NSG | 325 | 213 | 27.7 | 1-107/107orf | C. | C.H.B.S. |
| Annexin I | 34 | 1BO9 | 237 | 184 | 23.9 | 40-112/345orf | C.H. | C.H.B.S. |

TABLE 1-continued

| Gene | B #[1] | PDB[2] | Insert Length bp[3] | Fusion aa[4] | Fusion Kda[5] | Part Cloned[6] | Expression Vector 1 | Expression Vector 2 |
|---|---|---|---|---|---|---|---|---|
| Cyclophillin A | 36 | 1BCK | 495 | 270 | 35.1 | 1-164/164orf | C.H.B.S | C.H.B.S |
| Ser.-Thr. Phos. B-B | 41 | 1AUIB | 507 | 274 | 35.6 | 2-170/170orf | C. | C.H.B.S. |
| Transcr. Factor iib | 42 | 1TFB | 633 | 316 | 41.1 | 112-316/316orf | C. | C.H.B.S. |
| S-Admeth. Decarb. | 47 | 1JEN | 800 | 372 | 48.3 | 69-329/334orf | C. | C.H.B.S. |
| Procathepsin B | 49 | 3PBH | 948 | 421 | 54.7 | 19-333/339orf | C. | C.H.B.S. |
| Rhoa | 51 | 1CXZ | 561 | 292 | 38.0 | 1-181/193orf | C. | C.H.B.S. |
| Acid Phosphotase 1A | 51A | P24666 | 471 | 257 | 28.0 | 1-157/157orf | C. | C.H.B.S. |
| Pax-6 | 53 | 6PAX | 417 | 244 | 31.7 | 4-136/422orf | C. | C.H.B.S. |
| Phostyr. Phoslip | 55 | 5PNT | 492 | 269 | 35.0 | 1-157/157orf | C.H.B.S. | C.H.B.S. |
| Thyroid Hormone BP | 57A | Q14894 | 942 | 314 | 45 | 1-314/314orf | C. | C.H.B.S. |
| Hsp86 | 58A | — | 684 | 333 | 43.3 | 8-235/731orf | C.H.B.S. | C.H.B.S. |
| Hsp40 | 59 | 1HDJ | 231 | 182 | 23.7 | 1-76/340orf | C. | C.H.B.S. |
| NKκB52 | 61 | 1A3Q | 891 | 402 | 52.3 | 37-327/898orf | C.H.B.S. | C.H.B.S. |
| Fruc.-Bisph. Aid.* | 64 | 1DOS | 1095 | 470 | 61.1 | 1-358/358orf | C.H.B.S. | C.H.B.S. |
| Fadd | 65 | 1E3Y | 312 | 209 | 27.2 | 93-192/208orf | C. | C.H.B.S. |
| Transcr. Factor Max | 66 | 1HLO | 285 | 200 | 26.0 | 4-92/160orf | C. | C.H.B.S. |
| IL-6 | 67 | 2IL6 | 515 | 276.7 | 36.0 | 47-212/212orf | C.H. | C.H.B.S. |
| Hyp.-Guan. Phribtr. | 71 | 1NST | 660 | 325 | 42.3 | 4-217/217orf | C. | C.H.B.S. |
| Glyoxylase II | 78 | 1QH5 | 198 | 371 | 48.2 | 1-260/260orf | C. | C.H.B. |
| Srebp-1a | 80 | 1AM9 | 258 | 191 | 24.8 | 319-398/1147orf | C. | C.H.B.S. |

The invention claimed is:

1. A library of more than one correctly folded proteins encoded by two or more different coding sequences, wherein each of said proteins is fused at the N- or C-terminus to an identical BCCP (Biotin Carboxyl Carrier Protein) biotinylation domain, wherein the biotinylation domain is correctly folded; and wherein the biotinylation domain consists of the sequence:

AAAEISGHIVRSPMVGTFYRTPSP-
DAKAFIEVGQKVNVGDTLCIVEAMKM
MNQIEADKSGTVKAILVESGQPVEFDEPLVVIE
(SEQ ID NO:2).

2. The library as claimed in claim 1, wherein said BCCP is *E. coli* BCCP.

3. The library as claimed in claim 1, wherein said proteins are soluble.

4. The library as claimed in claim 1, wherein said proteins are immobilized on a solid substrate by said biotinylated domain to form an array, wherein the solid substrate comprises a surface selected from the group consisting of avidin, strepavidin or a deglycosylated avidin.

5. The library of claim 1, wherein the solubility of the more than one correctly folded proteins in the claimed library is increased relative to the solubility of the same more than one proteins in a library of proteins that have not been modified by fusion to the biotinylation domain.

6. A method of making the protein library of claim 1, comprising the step of generating a library of nucleic acid molecules encoding proteins of interest wherein each coding sequence is modified to incorporate a tag moiety comprising the biotinylation domain at the N-terminus or C-terminus of the encoded protein.

7. The method of claim 6, comprising the step of increasing the proportion of clones in the library of nucleic acid molecules expressing a protein of interest by
  a) attaching a first nucleic acid molecule encoding a tag moiety comprising the biotinylation domain 5' to and in-frame with
  b) a second nucleic acid molecule encoding each protein of interest, such that when the protein is expressed the tag moiety is located at the N-terminus of each protein.

8. A method of monitoring protein folding by measuring the extent of in vivo biotinylation of one or more of the proteins in the library of claim 1, wherein the amount of biotinylation is proportional to protein folding.

9. A method of determining the folded state of one or more proteins of interest in the library of claim 1 by detecting the presence or absence of biotin on the one or more proteins of interest, wherein the presence of biotin indicates that a protein is correctly folded and the absence of biotin indicates that the protein is misfolded or aggregated.

10. A library of nucleic acid molecules for producing the library of claim 1, wherein each coding sequence of the library of nucleic acid molecules is modified to incorporate a tag moiety comprising the biotinylation domain at the N-terminus or C-terminus of the encoded protein.

* * * * *

SEQUENCE LISTING

<160> NUMBER OF SEQ ID NOS: 35

<210> SEQ ID NO 1
<211> LENGTH: 252
<212> TYPE: DNA
<213> ORGANISM: Escherichia coli

<400> SEQUENCE: 1

```
gcagcagcgg aaatcagtgg tcacatcgta cgttccccga tggttggtac tttctaccgc      60
accccaagcc cggacgcaaa agcgttcatc gaagtgggtc agaaagtcaa cgtgggcgat     120
accctgtgca tcgttgaagc catgaaaatg atgaaccaga tcgaagcgga caaatccggt     180
accgtgaaag caattctggt cgaaagtgga caaccggtag aatttgacga gccgctggtc     240
gtcatcgagt aa                                                         252
```

<210> SEQ ID NO 2
<211> LENGTH: 83
<212> TYPE: PRT
<213> ORGANISM: Escherichia coli

<400> SEQUENCE: 2

```
Ala Ala Ala Glu Ile Ser Gly His Ile Val Arg Ser Pro Met Val Gly
1               5                   10                  15

Thr Phe Tyr Arg Thr Pro Ser Pro Asp Ala Lys Ala Phe Ile Glu Val
                20                  25                  30

Gly Gln Lys Val Asn Val Gly Asp Thr Leu Cys Ile Val Glu Ala Met
            35                  40                  45

Lys Met Met Asn Gln Ile Glu Ala Asp Lys Ser Gly Thr Val Lys Ala
        50                  55                  60

Ile Leu Val Glu Ser Gly Gln Pro Val Glu Phe Asp Glu Pro Leu Val
65                  70                  75                  80
```

Val Ile Glu

<210> SEQ ID NO 3
<211> LENGTH: 180
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 3
attgtgagcg gataacaatt tcacacagaa ttcattaaag aggagaaatt aactatgcac    60
ttagtgggat ccgcatgcga gctcggtacc ccgggccggt ggcagcgcga gtaaaggaga   120
agaacttttc actggagttg tcccaattct tgttgaatta gatggtgatg ttaatgggca   180

<210> SEQ ID NO 4
<211> LENGTH: 180
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 4
attgtgagcg gataacaatt tcacacagaa ttcattaaag aggagaaatt aactatggca    60
cttagtggga tccgcatgcg agctcggtac cccgggccgg tggcagcgcg agtaaaggag   120
aagaactttt cactggagtt gtcccaattc ttgttgaatt agatggtgat gttaatgggc   180

<210> SEQ ID NO 5
<211> LENGTH: 180
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 5
attgtgagcg gataacaatt tcacacagaa ttcattaaag aggagaaatt aactatggac    60
acttagtggg atccgcatgc gagctcggta ccccgggccg gtggcagcgc gagtaaagga   120
gaagaacttt tcactggagt tgtcccaatt cttgttgaat tagatggtga tgttaatggg   180

<210> SEQ ID NO 6
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gatggatccg atattcgtaa gattaaaaaa ctgatcg                             37

<210> SEQ ID NO 7
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gatgagctca agcttttact cgatgacgac cagcggctcg tc                       42

<210> SEQ ID NO 8
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gatctgcagg gctccgcagc agcggaaatc agtggtcaca tcg          43

<210> SEQ ID NO 9
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
catagttaat ttctcctctt taatgaattc tg          32

<210> SEQ ID NO 10
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gcggccgcgg ccattacggc cggatccgca tgcgagctcg gtacccc          48

<210> SEQ ID NO 11
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gggccggtgg cagcgcgagt aaaggagaag aactttcac tgg          43

<210> SEQ ID NO 12
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gatctgcagg gtaccggatc ctttgtagag ctcatccatg cc          42

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tcccctatac taggttattg g          21

-continued

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 14
gggcgtcacg atgaattccc ggg 23

<210> SEQ ID NO 15
<211> LENGTH: 35
<212> TYPE: DNA
<213> ORGANISM: Artificial Sequence
<220> FEATURE:
<223> OTHER INFORMATION: Description of Artificial Sequence: Synthetic
primer

<400> SEQUENCE: 15
cacttagtgg gatccgcatg cgagctcggt acccc 35

<210> SEQ ID NO 16
<211> LENGTH: 41
<212> TYPE: DNA
<213> ORGANISM: Artificial Sequence
<220> FEATURE:
<223> OTHER INFORMATION: Description of Artificial Sequence: Synthetic
primer

<400> SEQUENCE: 16
atgctcatga ggccggccgg gaattcggcc attacggccg g 41

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 17
gtctagaaag cttctcgagg gccg 24

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 18
tgatagaaga gcggccgc 18

<210> SEQ ID NO 19
<211> LENGTH: 598
<212> TYPE: PRT
<213> ORGANISM: Mycobacterium leprae

<400> SEQUENCE: 19

```
Met Ala Ser His Ala Ser Ser Arg Ile Ala Lys Val Leu Val Ala Asn
1               5                   10                  15

Arg Gly Glu Ile Ala Val Arg Val Ile Arg Ala Ala Arg Asp Ala Arg
            20                  25                  30

Leu Pro Ser Val Ala Val Tyr Ala Glu Pro Asp Ala Glu Ala Pro His
```

```
                35                  40                  45
Val Arg Leu Ala Asp Glu Ala Phe Ala Leu Gly Gly His Thr Ser Ala
 50                  55                  60

Glu Ser Tyr Leu Asp Phe Gly Lys Ile Leu Asp Ala Ala Lys Ser
65                   70                  75                  80

Gly Ala Asn Ala Ile His Pro Gly Tyr Gly Phe Leu Ala Glu Asn Ala
                 85                  90                  95

Asp Phe Ala Gln Ala Val Ile Asp Ala Gly Leu Ile Trp Ile Gly Pro
                100                 105                 110

Ser Pro Gln Ser Ile Arg Asp Leu Gly Asp Lys Val Thr Ala Arg His
                115                 120                 125

Ile Ala Ala Arg Ala Gln Ala Pro Leu Val Pro Gly Thr Pro Asp Pro
130                 135                 140

Val Lys Asn Ala Asp Glu Val Val Ala Phe Ala Lys Glu His Gly Val
145                 150                 155                 160

Pro Ile Ala Ile Lys Ala Ala Phe Gly Gly Gly Gly Lys Gly Met Lys
                165                 170                 175

Val Ala Arg Thr Leu Glu Glu Ile Ser Glu Leu Tyr Glu Ser Ala Val
                180                 185                 190

Arg Glu Ala Thr Val Ala Phe Gly Arg Gly Glu Cys Phe Val Glu Arg
                195                 200                 205

Tyr Leu Asp Lys Pro Arg His Val Glu Ala Gln Val Ile Ala Asp Gln
210                 215                 220

His Gly Asn Ile Val Val Ala Gly Thr Arg Asp Cys Ser Leu Gln Arg
225                 230                 235                 240

Arg Phe Gln Lys Leu Val Glu Glu Ala Pro Ala Pro Phe Leu Thr Asp
                245                 250                 255

Ala Gln Arg Lys Glu Ile His Glu Ser Ala Lys Arg Ile Cys Lys Glu
                260                 265                 270

Ala His Tyr Tyr Gly Ala Gly Thr Val Glu Tyr Leu Val Gly Gln Asp
                275                 280                 285

Gly Leu Ile Ser Phe Leu Glu Val Asn Thr Arg Leu Gln Val Glu His
290                 295                 300

Pro Val Thr Glu Glu Thr Thr Gly Ile Asp Leu Val Leu Gln Gln Phe
305                 310                 315                 320

Lys Ile Ala Asn Gly Glu Lys Leu Glu Leu Ile Lys Asp Pro Ile Pro
                325                 330                 335

Cys Gly His Ala Ile Glu Phe Arg Ile Asn Gly Glu Asp Ala Gly Arg
                340                 345                 350

Asn Phe Leu Pro Ser Pro Gly Pro Val Ser Lys Phe His Pro Pro Thr
                355                 360                 365

Gly Pro Gly Val Arg Leu Asp Ser Gly Val Glu Thr Gly Ser Val Ile
                370                 375                 380

Gly Gly Gln Phe Asp Ser Met Leu Ala Lys Leu Ile Val His Gly Ala
385                 390                 395                 400

Thr Arg Gln Glu Ala Leu Ala Arg Ala Arg Arg Ala Leu Asp Glu Phe
                405                 410                 415

Glu Val Glu Gly Leu Ala Thr Val Ile Pro Phe His Arg Ala Val Val
                420                 425                 430

Ser Asp Pro Ala Leu Ile Gly Asp Asn Asn Ser Phe Ser Val His Thr
                435                 440                 445

Arg Trp Ile Glu Thr Glu Trp Asn Asn Thr Ile Glu Pro Phe Ile Asp
450                 455                 460
```

```
Asn Gln Pro Leu Asp Glu Asp Thr Arg Pro Gln Gln Thr Val Ile
465                 470                 475                 480

Val Glu Val Asp Gly Arg Arg Leu Glu Val Ser Leu Pro Ala Asp Leu
            485                 490                 495

Ala Leu Ala Asn Pro Ala Gly Cys Asn Pro Ala Gly Val Ile Arg Lys
                500                 505                 510

Lys Pro Lys Pro Arg Lys Arg Gly Gly His Thr Gly Ala Ala Thr Ser
        515                 520                 525

Gly Asp Ala Val Thr Ala Pro Met Gln Gly Thr Val Val Lys Val Ala
        530                 535                 540

Val Ala Glu Gly Gln Thr Val Met Thr Gly Asp Leu Val Val Val Leu
545                 550                 555                 560

Glu Ala Met Lys Met Glu Asn Pro Val Thr Ala His Lys Asp Gly Ile
                565                 570                 575

Ile Thr Gly Leu Ala Val Glu Ala Gly Thr Ala Ile Thr Gln Gly Thr
                580                 585                 590

Val Leu Ala Glu Ile Lys
        595

<210> SEQ ID NO 20
<211> LENGTH: 654
<212> TYPE: PRT
<213> ORGANISM: Mycobacterium tuberculosis

<400> SEQUENCE: 20

Met Phe Asp Thr Val Leu Val Ala Asn Arg Gly Glu Ile Ala Val Arg
1               5                   10                  15

Val Ile Arg Thr Leu Arg Arg Leu Gly Ile Arg Ser Val Ala Val Tyr
            20                  25                  30

Ser Asp Pro Asp Val Asp Ala Arg His Val Leu Glu Ala Asp Ala Ala
        35                  40                  45

Val Arg Leu Gly Pro Ala Pro Ala Arg Glu Ser Tyr Leu Asp Ile Gly
    50                  55                  60

Lys Val Leu Asp Ala Ala Ala Arg Thr Gly Ala Gln Ala Ile His Pro
65                  70                  75                  80

Gly Tyr Gly Phe Leu Ala Glu Asn Ala Asp Phe Ala Ala Ala Cys Glu
                85                  90                  95

Arg Ala Arg Val Val Phe Leu Gly Pro Pro Ala Arg Ala Ile Glu Val
            100                 105                 110

Met Gly Asp Lys Ile Ala Ala Lys Asn Ala Val Ala Ala Phe Asp Val
        115                 120                 125

Pro Val Val Pro Gly Val Ala Arg Ala Gly Leu Thr Asp Asp Ala Leu
    130                 135                 140

Val Thr Ala Ala Ala Glu Val Gly Tyr Pro Val Leu Ile Lys Pro Ser
145                 150                 155                 160

Ala Gly Gly Gly Gly Lys Gly Met Arg Leu Val Gln Asp Pro Ala Arg
                165                 170                 175

Leu Pro Glu Ala Leu Val Ser Ala Arg Arg Glu Ala Met Ser Ser Phe
            180                 185                 190

Gly Asp Asp Thr Leu Phe Leu Glu Arg Phe Val Leu Arg Pro Arg His
        195                 200                 205

Ile Glu Val Gln Val Leu Ala Asp Ala His Gly Asn Val Val His Leu
    210                 215                 220

Gly Glu Arg Glu Cys Ser Leu Gln Arg Arg His Gln Lys Val Ile Glu
```

```
            225                 230                 235                 240
Glu Ala Pro Ser Pro Leu Leu Asp Pro Gln Thr Arg Glu Arg Ile Gly
                245                 250                 255

Val Ala Ala Cys Asn Thr Ala Arg Cys Val Asp Tyr Val Gly Ala Gly
                260                 265                 270

Thr Val Glu Phe Ile Val Ser Ala Gln Arg Pro Asp Glu Phe Phe Phe
                275                 280                 285

Met Glu Met Asn Thr Arg Leu Gln Val Glu His Pro Val Thr Glu Ala
                290                 295                 300

Ile Thr Gly Leu Asp Leu Val Glu Trp Gln Leu Arg Val Gly Ala Gly
305                 310                 315                 320

Glu Lys Leu Gly Phe Ala Gln Asn Asp Ile Glu Leu Arg Gly His Ala
                325                 330                 335

Ile Glu Ala Arg Val Tyr Ala Glu Asp Pro Ala Arg Glu Phe Leu Pro
                340                 345                 350

Thr Gly Gly Arg Val Leu Ala Val Phe Glu Pro Ala Gly Pro Gly Val
                355                 360                 365

Arg Val Asp Ser Ser Leu Leu Gly Gly Thr Val Val Gly Ser Asp Tyr
                370                 375                 380

Asp Pro Leu Leu Thr Lys Val Ile Ala His Gly Ala Asp Arg Glu Glu
385                 390                 395                 400

Ala Leu Asp Arg Leu Asp Gln Ala Leu Ala Arg Thr Ala Val Leu Gly
                405                 410                 415

Val Gln Thr Asn Val Glu Phe Leu Arg Phe Leu Leu Ala Asp Glu Arg
                420                 425                 430

Val Arg Val Gly Asp Leu Asp Thr Ala Val Leu Asp Glu Arg Ser Ala
                435                 440                 445

Asp Phe Thr Ala Arg Pro Ala Pro Asp Val Leu Ala Ala Gly Gly
                450                 455                 460

Leu Tyr Arg Gln Trp Ala Leu Ala Arg Ala Gln Gly Asp Leu Trp
465                 470                 475                 480

Ala Ala Pro Ser Gly Trp Arg Gly Gly His Met Ala Pro Val Arg
                485                 490                 495

Thr Ala Met Arg Thr Pro Leu Arg Ser Glu Thr Val Ser Val Trp Gly
                500                 505                 510

Pro Pro Glu Ser Ala Gln Val Gln Val Gly Asp Gly Glu Ile Asp Cys
                515                 520                 525

Ala Ser Val Gln Val Thr Arg Glu Gln Met Ser Val Thr Ile Ser Gly
530                 535                 540

Leu Arg Arg Asp Tyr Arg Trp Ala Glu Ala Asp Arg His Leu Trp Ile
545                 550                 555                 560

Ala Asp Glu Arg Gly Thr Trp His Leu Arg Glu Ala Glu Glu His Lys
                565                 570                 575

Ile His Arg Ala Val Gly Ala Arg Pro Ala Glu Val Val Ser Pro Met
                580                 585                 590

Pro Gly Ser Val Ile Ala Val Gln Val Glu Ser Gly Ser Gln Ile Ser
                595                 600                 605

Ala Gly Asp Val Val Val Val Glu Ala Met Lys Met Glu His Ser
                610                 615                 620

Leu Glu Ala Pro Val Ser Gly Arg Val Gln Val Leu Ser Val Gly
625                 630                 635                 640

Asp Gln Val Lys Val Glu Gln Val Leu Ala Arg Ile Lys Asp
                645                 650
```

<210> SEQ ID NO 21
<211> LENGTH: 181
<212> TYPE: PRT
<213> ORGANISM: Nostoc sp. (strain PCC 7120 / UTEX 2576)

<400> SEQUENCE: 21

| Pro | Leu | Asp | Phe | Asn | Glu | Ile | Arg | Gln | Leu | Leu | Thr | Thr | Ile | Ala | Gln |
|---|---|---|---|---|---|---|---|---|---|---|---|---|---|---|---|
| 1 | | | | 5 | | | | | 10 | | | | | 15 | |

Thr Asp Ile Ala Glu Val Thr Leu Lys Ser Asp Asp Phe Glu Leu Thr
            20                  25                  30

Val Arg Lys Ala Val Gly Val Asn Asn Ser Val Val Pro Val Val Thr
        35                  40                  45

Ala Pro Leu Ser Gly Val Val Gly Ser Gly Leu Pro Ser Ala Ile Pro
    50                  55                  60

Ile Val Ala His Ala Ala Pro Ser Pro Ser Pro Glu Pro Gly Thr Ser
65                  70                  75                  80

Arg Ala Ala Asp His Ala Val Thr Ser Ser Gly Ser Gln Pro Gly Ala
                85                  90                  95

Lys Ile Ile Asp Gln Lys Leu Ala Glu Val Ala Ser Pro Met Val Gly
            100                 105                 110

Thr Phe Tyr Arg Ala Pro Ala Pro Gly Glu Ala Val Phe Val Glu Val
        115                 120                 125

Gly Asp Arg Ile Arg Gln Gly Gln Thr Val Cys Ile Ile Glu Ala Met
    130                 135                 140

Lys Leu Met Asn Glu Ile Glu Ala Asp Val Ser Gly Gln Val Ile Glu
145                 150                 155                 160

Ile Leu Val Gln Asn Gly Glu Pro Val Glu Tyr Asn Gln Pro Leu Met
                165                 170                 175

Arg Ile Lys Pro Asp
            180

<210> SEQ ID NO 22
<211> LENGTH: 280
<212> TYPE: PRT
<213> ORGANISM: Arabidopsis thaliana

<400> SEQUENCE: 22

Met Ala Ser Ser Ser Phe Ser Val Thr Ser Pro Ala Ala Ala Ala Ser
1               5                   10                  15

Val Tyr Ala Val Thr Gln Thr Ser Ser His Phe Pro Ile Gln Asn Arg
            20                  25                  30

Ser Arg Arg Val Ser Phe Arg Leu Ser Ala Lys Pro Lys Leu Arg Phe
        35                  40                  45

Leu Ser Lys Pro Ser Arg Ser Ser Tyr Pro Val Val Lys Ala Gln Ser
    50                  55                  60

Asn Lys Val Ser Thr Gly Ala Ser Ser Asn Ala Ala Lys Val Asp Gly
65                  70                  75                  80

Pro Ser Ser Ala Glu Gly Lys Glu Lys Asn Ser Leu Lys Glu Ser Ser
                85                  90                  95

Ala Ser Pro Glu Leu Ala Thr Glu Glu Ser Ile Ser Glu Phe Leu
            100                 105                 110

Thr Gln Val Thr Thr Leu Val Lys Leu Val Asp Ser Arg Asp Ile Val
        115                 120                 125

Glu Leu Gln Leu Lys Gln Leu Asp Cys Glu Leu Val Ile Arg Lys Lys
    130                 135                 140

```
Glu Ala Leu Pro Gln Pro Gln Ala Pro Ala Ser Tyr Val Met Met Gln
145                 150                 155                 160

Gln Pro Asn Gln Pro Ser Tyr Ala Gln Gln Met Ala Pro Pro Ala Ala
                165                 170                 175

Pro Ala Ala Ala Ala Pro Ala Pro Ser Thr Pro Ala Ser Leu Pro Pro
            180                 185                 190

Pro Ser Pro Pro Thr Pro Ala Lys Ser Ser Leu Pro Thr Val Lys Ser
        195                 200                 205

Pro Met Ala Gly Thr Phe Tyr Arg Ser Pro Ala Pro Gly Glu Pro Pro
    210                 215                 220

Phe Ile Lys Val Gly Asp Lys Val Gln Lys Gly Gln Val Leu Cys Ile
225                 230                 235                 240

Val Glu Ala Met Lys Leu Met Asn Glu Ile Glu Ser Asp His Thr Gly
                245                 250                 255

Thr Val Val Asp Ile Val Ala Glu Asp Gly Lys Pro Val Ser Leu Asp
            260                 265                 270

Thr Pro Leu Phe Val Val Gln Pro
        275                 280

<210> SEQ ID NO 23
<211> LENGTH: 159
<212> TYPE: PRT
<213> ORGANISM: Bacillus subtilis

<400> SEQUENCE: 23

Met Leu Asn Ile Lys Glu Ile His Glu Leu Ile Lys Ala Ile Asp Glu
1               5                   10                  15

Ser Thr Ile Asp Glu Phe Val Tyr Glu Asn Glu Gly Val Ser Leu Lys
            20                  25                  30

Leu Lys Lys His Glu Ala Gly Thr Val Gln Val Met Gln Gln Ala Pro
        35                  40                  45

Ala Ala Pro Val Gln Ala Gln Ala Pro Gln Ala Val Gln Pro Gln Ala
    50                  55                  60

Gln Gln Ala Ala Ala Pro Ala Gln Glu Ala Pro Lys Gln Asp Glu Asn
65                  70                  75                  80

Leu His Lys Ile Thr Ser Pro Met Val Gly Thr Phe Tyr Ala Ser Ser
                85                  90                  95

Ser Pro Glu Ala Gly Pro Tyr Val Thr Ala Gly Ser Lys Val Asn Glu
            100                 105                 110

Asn Thr Val Val Cys Ile Val Glu Ala Met Lys Leu Phe Ile Glu Ile
        115                 120                 125

Glu Ala Glu Val Lys Gly Glu Ile Val Glu Val Leu Val Glu Asn Gly
    130                 135                 140

Gln Leu Val Glu Tyr Gly Gln Pro Leu Phe Leu Val Lys Ala Glu
145                 150                 155

<210> SEQ ID NO 24
<211> LENGTH: 163
<212> TYPE: PRT
<213> ORGANISM: Chlamydia muridarum (strain MoPn / Nigg)

<400> SEQUENCE: 24

Met Asp Leu Lys Gln Ile Glu Lys Leu Met Ile Ala Met Gly Arg Asn
1               5                   10                  15

Lys Met Lys Arg Ile Ala Ile Lys Arg Asp Gly Phe Glu Leu Glu Leu
            20                  25                  30
```

```
Glu Arg Asp Thr Gly Pro Asn Ile Gln Glu Pro Val Phe Tyr Asp Asn
         35                  40                  45

Arg Leu Phe Ala Gly Phe Thr Gln Glu Arg Pro Ile Pro Ser Asp Gln
 50                  55                  60

Asn Leu Gly Asn Pro Ile Val Lys Glu Val Gly Glu Lys Lys Glu Asp
 65                  70                  75                  80

Lys Pro Val Glu Gly Asp Phe Ile Val Ser Pro Leu Val Gly Thr Phe
                 85                  90                  95

Tyr Gly Ala Pro Ser Pro Glu Ser Pro Ala Phe Val Lys Pro Gly Asp
                100                 105                 110

Ile Val Ser Glu Asp Thr Val Val Cys Ile Val Glu Ala Met Lys Val
        115                 120                 125

Met Asn Glu Val Lys Ala Gly Met Ala Gly Arg Val Glu Glu Val Leu
130                 135                 140

Ile Thr Asn Gly Asp Pro Val Gln Phe Gly Ser Lys Leu Phe Arg Ile
145                 150                 155                 160

Val Lys Ala

<210> SEQ ID NO 25
<211> LENGTH: 167
<212> TYPE: PRT
<213> ORGANISM: Chlamydia pneumoniae

<400> SEQUENCE: 25

Met Asp Leu Lys Gln Ile Glu Lys Leu Met Ile Ala Met Gly Arg Asn
 1               5                  10                  15

Gly Met Lys Arg Phe Ala Ile Lys Arg Glu Gly Leu Glu Leu Glu Leu
                 20                  25                  30

Glu Arg Asp Thr Arg Glu Gly Asn Arg Gln Glu Pro Val Phe Tyr Asp
         35                  40                  45

Ser Arg Leu Phe Ser Gly Phe Ser Gln Glu Arg Pro Ile Pro Thr Asp
 50                  55                  60

Pro Lys Lys Asp Thr Ile Lys Glu Thr Thr Glu Asn Ser Glu Thr
 65                  70                  75                  80

Ser Thr Thr Thr Ser Ser Gly Asp Phe Ile Ser Ser Pro Leu Val Gly
                 85                  90                  95

Thr Phe Tyr Gly Ser Pro Ala Pro Asp Ser Pro Ser Phe Val Lys Pro
                100                 105                 110

Gly Asp Ile Val Ser Glu Asp Thr Ile Val Cys Ile Val Glu Ala Met
        115                 120                 125

Lys Val Met Asn Glu Val Lys Ala Gly Met Ser Gly Arg Val Leu Glu
130                 135                 140

Val Leu Ile Thr Asn Gly Asp Pro Val Gln Phe Gly Ser Lys Leu Phe
145                 150                 155                 160

Arg Ile Ala Lys Asp Ala Ser
                165

<210> SEQ ID NO 26
<211> LENGTH: 164
<212> TYPE: PRT
<213> ORGANISM: Chlamydia trachomatis

<400> SEQUENCE: 26

Met Asp Leu Lys Gln Ile Glu Lys Leu Met Ile Ala Met Gly Arg Asn
 1               5                  10                  15
```

```
Lys Met Lys Arg Ile Val Ile Lys Arg Glu Gly Leu Glu Leu Leu
            20                  25                  30

Glu Arg Asp Thr Val Pro Ser Ile Gln Glu Pro Val Phe Tyr Asp Asn
        35                  40                  45

Arg Leu Phe Ala Gly Phe Ser Gln Arg Pro Ile Pro Thr Asp Gln
50                      55                  60

Asn Leu Gly Asn Pro Ile Val Lys Glu Ser Ile Lys Lys Glu Ser
65                  70                  75                  80

Glu Ala Pro Ala Gln Gly Asp Phe Ile Val Ser Pro Leu Val Gly Thr
                85                  90                  95

Phe Tyr Gly Ser Pro Ser Pro Glu Ala Pro Ala Phe Ile Lys Pro Gly
            100                 105                 110

Asp Thr Val Ser Glu Asp Thr Val Val Cys Ile Val Glu Ala Met Lys
            115                 120                 125

Val Met Asn Glu Val Lys Ala Gly Met Ser Gly Arg Val Glu Glu Ile
130                 135                 140

Leu Ile Thr Asn Gly Asp Pro Val Gln Phe Gly Ser Leu Phe Arg
145                 150                 155                 160

Ile Val Lys Ala

<210> SEQ ID NO 27
<211> LENGTH: 152
<212> TYPE: PRT
<213> ORGANISM: Cyanidium caldarium

<400> SEQUENCE: 27

Met Leu His Ser Ser Ile Tyr Trp Lys Asn Leu Ile Asn Thr Phe Glu
1               5                   10                  15

Ser Gly Cys Phe Ser Ile Ala Glu Val Lys Phe Ile Phe Ser Asn Ile
            20                  25                  30

His Ile Tyr Lys Asn Ile Cys Asn Pro Tyr Lys Asn Tyr Gln Leu Pro
        35                  40                  45

Glu Leu Ala Arg Asn Leu Gln Ser Ser Lys Lys Leu Asp Asn Ala Ile
50                  55                  60

Leu Lys Gln Asp Lys Lys Asn Ile Ile Asp Ile Leu Ser Pro Ile Ser
65                  70                  75                  80

Gly Ile Phe Tyr Ser Ser Ser Lys Pro Gly Ala Ser Pro Phe Val Ala
                85                  90                  95

Val Gly Ser Val Val Ser Lys Gly Gln Thr Leu Cys Ile Ile Glu Ala
            100                 105                 110

Met Lys Thr Met Asn Glu Ile Glu Ser Asp Ser Ile Gly Lys Ile His
            115                 120                 125

Gln Ile Cys Ala Arg Asn Gly Asp Phe Val Thr Lys Asn Gln Val Leu
130                 135                 140

Met Lys Ile Ile Leu Glu Gln Ser
145                 150

<210> SEQ ID NO 28
<211> LENGTH: 156
<212> TYPE: PRT
<213> ORGANISM: Escherichia coli

<400> SEQUENCE: 28

Met Asp Ile Arg Lys Ile Lys Lys Leu Ile Glu Leu Val Glu Glu Ser
1               5                   10                  15

Gly Ile Ser Glu Leu Glu Ile Ser Glu Gly Glu Glu Ser Val Arg Ile
```

```
                20                  25                  30
Ser Arg Ala Ala Pro Ala Ala Ser Phe Pro Val Met Gln Gln Ala Tyr
            35                  40                  45

Ala Ala Pro Met Met Gln Gln Pro Ala Gln Ser Asn Ala Ala Ala Pro
 50                  55                  60

Ala Thr Val Pro Ser Met Glu Ala Pro Ala Ala Glu Ile Ser Gly
 65                  70                  75                  80

His Ile Val Arg Ser Pro Met Val Gly Thr Phe Tyr Arg Thr Pro Ser
                85                  90                  95

Pro Asp Ala Lys Ala Phe Ile Glu Val Gly Gln Lys Val Asn Val Gly
            100                 105                 110

Asp Thr Leu Cys Ile Val Glu Ala Met Lys Met Met Asn Gln Ile Glu
        115                 120                 125

Ala Asp Lys Ser Gly Thr Val Lys Ala Ile Leu Val Glu Ser Gly Gln
    130                 135                 140

Pro Val Glu Phe Asp Glu Pro Leu Val Val Ile Glu
145                 150                 155

<210> SEQ ID NO 29
<211> LENGTH: 155
<212> TYPE: PRT
<213> ORGANISM: Haemophilus influenzae

<400> SEQUENCE: 29

Met Asp Ile Arg Lys Ile Lys Lys Leu Ile Glu Leu Val Glu Glu Ser
1               5                   10                  15

Gly Ile Thr Glu Leu Glu Val Gln Glu Glu Gly Thr Val Arg Ile
                20                  25                  30

Ser Arg Ala Ala Pro Val Ile Ala Pro Ala Ala Val Gln Tyr Ala Ala
            35                  40                  45

Ala Pro Val Val Ala Pro Thr Pro Ala Ala Pro Ala Gln Val Pro
 50                  55                  60

Ala Ala Ala Thr Thr Ala Pro Ala Ala Ser Asp Glu Leu Ser Gly His
 65                  70                  75                  80

Leu Val Arg Ser Pro Met Val Gly Thr Phe Tyr Arg Ser Pro Ser Pro
                85                  90                  95

Glu Ala Lys Ala Phe Val Glu Val Gly Gln Ser Val Lys Val Gly Asp
            100                 105                 110

Ala Leu Cys Ile Val Glu Ala Met Lys Met Met Asn Arg Ile Glu Ala
        115                 120                 125

Asp Lys Ala Gly Val Val Lys Ala Ile Leu Ile Asn Asp Gly Asn Ala
    130                 135                 140

Val Glu Phe Asp Glu Pro Leu Ile Val Ile Glu
145                 150                 155

<210> SEQ ID NO 30
<211> LENGTH: 70
<212> TYPE: PRT
<213> ORGANISM: Lycopersicon esculentum

<400> SEQUENCE: 30

Gly Thr Val Val Ala Pro Met Val Gly Leu Glu Val Lys Val Leu Val
1               5                   10                  15

Lys Asp Gly Glu Lys Val Gln Glu Gly Gln Pro Val Leu Val Leu Glu
                20                  25                  30

Ala Met Lys Met Glu His Val Val Lys Ala Pro Ala Asn Gly Tyr Val
```

```
                    35                  40                  45
Ser Gly Leu Glu Ile Lys Val Gly Gln Ser Val Gln Asp Gly Ile Lys
            50                  55                  60

Leu Phe Ala Leu Lys Asp
65                  70

<210> SEQ ID NO 31
<211> LENGTH: 157
<212> TYPE: PRT
<213> ORGANISM: Porphyra purpurea

<400> SEQUENCE: 31

Met Gln Ile Thr Ile Lys Asp Leu Gln Asp Leu Leu Ser Ser Val Gln
1               5                   10                  15

Arg Lys Lys Ile Gln Thr Leu Lys Leu Lys Lys Asn Lys Phe Glu Leu
            20                  25                  30

Ile Leu Asn Lys Pro Ser Lys Lys Val Pro Gln Glu Val Val Ser Leu
            35                  40                  45

Lys Ser Ser His Ile Phe Lys Ser Ile His Ser Glu Thr Ile Asn Ile
        50                  55                  60

Pro Pro Lys Lys Thr Glu Ser Ile Asn Ser Lys Pro Ser Thr Asn Tyr
65                  70                  75                  80

Ala Thr Ile Val Ser Pro Met Val Gly Thr Phe Tyr His Ser Pro Ala
                85                  90                  95

Pro Gly Glu Lys Ile Phe Val Gln Val Gly Asp Ile Val Lys Cys Asn
            100                 105                 110

Gln Thr Val Cys Ile Ile Glu Ala Met Lys Leu Met Asn Glu Ile Glu
        115                 120                 125

Ala Glu Ile Glu Gly Ile Ile Glu Ile Leu Val Lys Asn Gly Asp
    130                 135                 140

Ile Val Asp Cys Gly Gln Ala Leu Met Lys Val Glu Thr
145                 150                 155

<210> SEQ ID NO 32
<211> LENGTH: 123
<212> TYPE: PRT
<213> ORGANISM: Propionibacterium freudenreichii shermanii

<400> SEQUENCE: 32

Met Lys Leu Lys Val Thr Val Asn Gly Thr Ala Tyr Asp Val Asp Val
1               5                   10                  15

Asp Val Asp Lys Ser His Glu Asn Pro Met Gly Thr Ile Leu Phe Gly
            20                  25                  30

Gly Gly Thr Gly Gly Ala Pro Ala Pro Arg Ala Ala Gly Gly Ala Gly
            35                  40                  45

Ala Gly Lys Ala Gly Glu Gly Glu Ile Pro Ala Pro Leu Ala Gly Thr
        50                  55                  60

Val Ser Lys Ile Leu Val Lys Glu Gly Asp Thr Val Lys Ala Gly Gln
65                  70                  75                  80

Thr Val Leu Val Leu Glu Ala Met Lys Met Glu Thr Glu Ile Asn Ala
                85                  90                  95

Pro Thr Asp Gly Lys Val Glu Lys Val Leu Val Lys Glu Arg Asp Ala
            100                 105                 110

Val Gln Gly Gly Gln Gly Leu Ile Lys Ile Gly
        115                 120
```

-continued

```
<210> SEQ ID NO 33
<211> LENGTH: 156
<212> TYPE: PRT
<213> ORGANISM: Pseudomonas aeruginosa

<400> SEQUENCE: 33

Met Asp Ile Arg Lys Val Lys Lys Leu Ile Glu Leu Leu Glu Glu Ser
1               5                   10                  15

Gly Ile Asp Glu Leu Glu Ile Arg Glu Gly Glu Glu Ser Val Arg Ile
            20                  25                  30

Ser Arg His Ser Lys Thr Ala Ala Gln Pro Val Tyr Ala Gln Ala Pro
        35                  40                  45

Ala Phe Ala Ala Pro Val Ala Pro Ala Pro Ala Ala Ala Ala Ala Pro
    50                  55                  60

Ala Ala Ala Ala Glu Ser Ala Pro Ala Ala Pro Lys Leu Asn Gly Asn
65                  70                  75                  80

Asn Val Val Arg Ser Pro Met Val Gly Thr Phe Tyr Arg Ala Ala Ser
                85                  90                  95

Pro Thr Ser Ala Asn Phe Val Glu Val Gly Gln Ser Val Lys Lys Gly
            100                 105                 110

Asp Ile Leu Cys Ile Val Glu Ala Met Lys Met Met Asn His Ile Glu
        115                 120                 125

Ala Glu Val Ser Gly Thr Ile Glu Ser Ile Leu Val Glu Asn Gly Gln
    130                 135                 140

Pro Val Glu Phe Asp Gln Pro Leu Phe Thr Ile Val
145                 150                 155

<210> SEQ ID NO 34
<211> LENGTH: 262
<212> TYPE: PRT
<213> ORGANISM: Glycine max

<400> SEQUENCE: 34

Met Ala Ser Ser Leu Ala Pro Ala Thr Lys Ala Ala Thr Asn Leu Arg
1               5                   10                  15

Leu Thr His Ser Leu Arg Phe Ser Pro Lys Pro Asn Asn Leu Arg Phe
            20                  25                  30

Ala Thr Lys Pro Gly Asn Thr Leu Leu Cys Thr Arg Val Lys Ala Gln
        35                  40                  45

Leu Asn Glu Val Ala Leu Asp Ser Ser Ser Asn Ala Thr Ser Pro Pro
    50                  55                  60

Met Lys Ala Lys Ser Lys Glu Glu Pro Ala Lys Pro Leu Ala Glu
65                  70                  75                  80

Pro Ser Ser Ser Val Leu Ala Thr Gln Glu Ser Val Ser Gln Phe Ile
                85                  90                  95

Thr Gln Val Ala Ser Leu Val Lys Leu Val Asp Ser Arg Asp Ile Val
            100                 105                 110

Glu Leu Lys Leu Lys Gln His Asp Val Glu Val Thr Ile Arg Lys Lys
        115                 120                 125

Glu Ala Met Pro Gln Pro Pro Ala Pro Gln Pro Ser Val Val Tyr
    130                 135                 140

Ser Pro Pro Pro Pro Leu Pro Pro Pro Val Pro Ala Ser Thr
145                 150                 155                 160

Pro Ala Pro Thr Leu Ala Arg Ala Thr Pro Thr Pro Thr Ser Ala Pro
                165                 170                 175

Ala Val Lys Ser Ala Lys Ser Ser Leu Pro Pro Leu Lys Ser Pro Met
```

```
                        180               185               190
Ala Gly Thr Phe Tyr Arg Ser Pro Ala Pro Gly Glu Pro Ser Phe Val
            195               200               205

Lys Val Gly Asp Lys Val Lys Lys Gly Gln Val Val Cys Ile Ile Glu
        210               215               220

Ala Met Lys Leu Met Asn Glu Ile Glu Ala Asp Gln Ser Gly Thr Ile
225             230               235                   240

Val Glu Ile Val Ala Glu Asp Ala Lys Ser Val Ser Val Asp Thr Pro
                245               250               255

Leu Phe Val Ile Gln Pro
                260

<210> SEQ ID NO 35
<211> LENGTH: 130
<212> TYPE: PRT
<213> ORGANISM: Streptococcus mutans serotype c

<400> SEQUENCE: 35

Met Leu Arg Lys Phe Lys Ile Ser Ile Asp Gly Lys Glu Tyr Leu Val
1               5                   10                  15

Glu Met Glu Glu Ile Ser Glu Ser Ser Val Pro Ala Ala Thr Pro Ile
            20                  25                  30

Thr Pro Thr Thr Glu Asn Thr Arg Ala Ala Ser Asp Gln Lys Gln Gln
        35                  40                  45

Ser Gln Thr Pro Ser Pro Ala Ala Thr Ala Ser Ala Ala Asn Thr Met
    50                  55                  60

Pro Ala Pro Met Pro Gly Thr Ile Leu Lys Val Leu Val Asn Val Gly
65                  70                  75                  80

Asp Thr Val Ser Glu Asn Gln Pro Leu Met Ile Leu Glu Ala Met Lys
                85                  90                  95

Met Glu Asn Glu Ile Val Ala Gly Met Ala Gly Thr Val Ser Ala Ile
            100                 105                 110

His Val Ser Ser Gly Gln Thr Val Asp Ala Gly Asp Asn Leu Ile Thr
        115                 120                 125

Ile Ala
130
```